(12) United States Patent
Fevre et al.

(10) Patent No.: US 10,743,537 B2
(45) Date of Patent: Aug. 18, 2020

(54) MONOMER COMPOSITIONS WITH ANTIMICROBIAL FUNCTIONALITY

(71) Applicants: International Business Machines Corporation, Armonk, NY (US); Agency for Science, Technology and Research, Connexis (SG)

(72) Inventors: Mareva B. Fevre, San Jose, CA (US); James L. Hedrick, Pleasanton, CA (US); Nathaniel H. Park, San Jose, CA (US); Victoria A. Piunova, Los Gatos, CA (US); Pang Kern Jeremy Tan, Singapore (SG); Yi Yan Yang, Singapore (SG); Mu San Zhang, San Francisco, CA (US)

(73) Assignees: INTERNATIONAL BUSINESS MACHINES CORPORATION, Armonk, NY (US); AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 79 days.

(21) Appl. No.: 15/839,199

(22) Filed: Dec. 12, 2017

(65) Prior Publication Data
US 2019/0174757 A1    Jun. 13, 2019

(51) Int. Cl.
| | |
|---|---|
| A01N 37/30 | (2006.01) |
| A01N 43/50 | (2006.01) |
| C07C 231/12 | (2006.01) |
| C07C 233/78 | (2006.01) |
| C07D 233/61 | (2006.01) |
| A01N 33/12 | (2006.01) |

(52) U.S. Cl.
CPC ............. *A01N 37/30* (2013.01); *A01N 33/12* (2013.01); *A01N 43/50* (2013.01); *C07C 231/12* (2013.01); *C07C 233/78* (2013.01); *C07D 233/61* (2013.01)

(58) Field of Classification Search
CPC ........ A01N 37/30; A01N 33/12; A01N 43/50; C07C 231/12; C07C 233/78; C07D 233/61
See application file for complete search history.

(56) References Cited

U.S. PATENT DOCUMENTS

| | | | |
|---|---|---|---|
| 3,632,623 A | * | 1/1972 | Becke |
| 4,013,507 A | | 3/1977 | Rembaum |
| 4,032,596 A | * | 6/1977 | Uffner |
| 4,094,827 A | | 6/1978 | McEntire |
| 4,166,894 A | | 9/1979 | Schaper |
| 4,348,536 A | | 9/1982 | Blahak et al. |
| 4,698,391 A | * | 10/1987 | Yacobucci |
| 4,794,031 A | | 12/1988 | Leir et al. |
| 4,883,655 A | * | 11/1989 | Login |
| 5,419,897 A | | 5/1995 | Drake et al. |
| 5,681,862 A | | 10/1997 | Hollis et al. |
| 6,767,549 B2 | | 7/2004 | Mandeville, III et al. |
| 6,955,806 B2 | | 10/2005 | Fitzpatrick et al. |
| 8,541,477 B2 | | 9/2013 | Alabdulrahman et al. |
| 2006/0002889 A1 | | 1/2006 | Fitzpatrick |
| 2007/0025954 A1 | | 2/2007 | Fitzpatrick et al. |
| 2007/0106061 A1 | | 5/2007 | Zollinger et al. |
| 2012/0202979 A1 | | 8/2012 | Wu |
| 2013/0281515 A1 | | 10/2013 | Coady et al. |
| 2014/0275469 A1 | | 9/2014 | Dhal et al. |
| 2015/0038392 A1 | | 2/2015 | Scheuing et al. |
| 2016/0374335 A1 | | 12/2016 | Chan et al. |
| 2016/0375150 A1 | | 12/2016 | Wu |

FOREIGN PATENT DOCUMENTS

| | | |
|---|---|---|
| CN | 1192649 A | 9/1998 |
| CN | 1254334 A | 5/2000 |
| CN | 1518621 A | 8/2004 |
| CN | 101426507 A | 5/2009 |
| CN | 101646728 A | 2/2010 |
| CN | 105482105 A | 4/2016 |
| GB | 2 000 164 A | 1/1979 |
| JP | H103255139 A | 11/1991 |
| JP | 2004224734 * | 8/2004 |
| JP | 2008214529 A | 9/2008 |
| WO | 97/02744 A1 | 1/1997 |
| WO | 98/54140 A1 | 12/1998 |
| WO | 02/080939 A2 | 10/2002 |
| WO | 02/099192 A2 | 12/2002 |
| WO | 2016/178634 A1 | 11/2016 |
| WO | 2016/186581 A1 | 11/2016 |
| WO | 2016/209732 A1 | 12/2016 |

OTHER PUBLICATIONS

Tiecco et al. (Colloids and Surfaces B: Biointerface, vol. 111, pp. 407-417, Published Nov. 2013 (Year: 2013).*

(Continued)

*Primary Examiner* — Alma Pipic
(74) *Attorney, Agent, or Firm* — Amin, Turocy & Watson, LLP

(57) ABSTRACT

Techniques regarding ionene compositions with antimicrobial functionality are provided. For example, one or more embodiments can comprise a monomer, which can comprise a single ionene unit. The single ionene unit can comprise a cation distributed along a molecular backbone. Also, a hydrophobic functional group can be covalently bonded to the molecular backbone, and the single ionene unit can have antimicrobial functionality.

8 Claims, 15 Drawing Sheets

(56) References Cited

OTHER PUBLICATIONS

Ol'Khovik et al. (Russian Journal of General Chemistry, vol. 83, No. 2, Published 2013, pp. 329-335) (Year: 2013).*

Wynne et al. (Applied Materials and Interfaces, Published 2011, pp. 2005-2011) (Year: 2011).*

Menger et al. (Langmuir, published 1996, pp. 1471-1473) (Year: 1996).*

Jones (Journal of Organic Chemistry, vol. 27, pp. 806-814, Published 1962) (Year: 1962).*

Haque et al. (Hindawi Publishing Corporation Journal of Chemistry, Published 2013, pp. 1-11) (Year: 2013).*

Liu, et al., Highly potent antimicrobial polyionenes with rapid killing kinetics, skin biocompatibility and in vivo bactericidal activity, Biomaterials, 2017, pp. 36-48, vol. 127.

Williams, et al., Recent advances in the synthesis and structure—property relationships of ammonium ionenes, Progress in Polymer Science, 2009, pp. 762-782, vol. 34.

Narita, et al., Effects of charge density and hydrophobicity of ionene polymer on cell binding and viability, Colloid Polym. Sci, 2000, pp. 884-887.

Mattheis, et al., Closing One of the Last Gaps in Polyionene Compositions: Alkyloxyethylammonium Ionenes as Fast-Acting Biocides, Macromolecular Bioscience, 2012, pp. 341-349, vol. 12.

Strassburg, et al., Nontoxic, Hydrophilic Cationic Polymers—Identified as Class of Antimicrobial Polymers, Macromolecular Bioscience, 2015, pp. 1710-1723, vol. 15.

Mayr, et al., Antimicrobial and Hemolytic Studies of a Series of Polycations Bearing Quaternary Ammonium Moieties: Structural and Topological Effects, International Journal of Molecular Sciences, 2017, 8 pages, vol. 18, No. 303.

Tamami, Synthesis and Characterization of Ammonium Ionenes Containing Hydrogen Bonding Functionalities, Dec. 6, 2012, 108 pages, Virginia Polytechnic Institute and State University.

Brown et al., The Structure Activity Relationship of Urea Derivatives as Anti-Tuberculosis Agents, Bioorg Med Chem. Sep. 15, 2011, pp. 5585-5595 vol. 19, No. 18.

Williams, Influence of Electrostatic Interactions and Hydrogen Bonding on the Thermal and Mechanical Properties of Step-Growth Polymers, Oct. 21, 2008, 375 pages, Virginia Polytechnic Institute and State University.

List of IBM Patents or Applications Treated as Related.

International Search Report and Written Opinion received for PCT Application Serial No. PCT/IB2018/059622, dated Mar. 28, 2019, 9 pages.

International Search Report and Written Opinion received for PCT Application Serial No. PCT/IB2018/059626, dated Apr. 15, 2019, 8 pages.

International Search Report and Written Opinion received for PCT Application Serial No. PCT/IB2018/059620, dated Mar. 27, 2019, 11 pages.

International Search Report and Written Opinion received for PCT Application Serial No. PCT/IB2018/059624 dated Apr. 17, 2019, 8 pages.

Non-Final Office Action received for U.S. Appl. No. 15/839,388 dated Jul. 10, 2019, 52 pages.

Murakami et al., "Syntheses of Macrocyclic Enzyme Models, Part 4. Preparation and Characterization of Cationic Octopus Azaparacyclophanes", Organic and Bio-Organic Chemistry, Journal of the Chemical Society, Perkin Transactions 1, Issue 11, Jan. 1, 1981, pp. 2800-2808.

Non-Final Office Action received for U.S. Appl. No. 15/839,415 dated Jul. 10, 2019, 29 pages.

International Search Report and Written Opinion received for PCT Application Serial No. PCT/IB2018/059621 dated Apr. 10, 2019, 8 pages.

Non-Final Office Action received for U.S. Appl. No. 15/839,402 dated Jun. 26, 2019, 56 pages.

Odagi et al., "Origin of Stereocontrol in Guanidine-Bisurea Bifunctional Organocatalyst That Promotes α-Hydroxylation of Tetralone-Derived β-Ketoesters: Asymmetric Synthesis of β- and γ-Substituted Tetralone Derivatives via Organocatalytic Oxidative Kinetic Resolution", Journal of the American Chemical Society, Jan. 2015, pp. 1909-1915.

Magri et al., "Rethinking the old antiviral drug moroxydine: Discovery of novel analogues as anti-hepatitis C virus (HCV) agents", Bioorganic and Medicinal Chemistry Letters, vol. 25, No. 22, Nov. 2015, pp. 5372-5376.

Non-Final Office Action received for U.S. Appl. No. 15/839,270 dated Sep. 16, 2019, 70 pages.

Non-Final Office Action received for U.S. Appl. No. 15/839,397 dated Sep. 17, 2019, 47 pages.

Wettig et al., "Thermodynamic and aggregation properties of aza- and imino-substituted gemini surfactants designed or gene delivery", Physical Chemistry Chemical Physics, vol. 9, 2007, pp. 871-877.

Notice of Allowance received for U.S. Appl. No. 15/839,402 dated Oct. 24, 2019, 113 pages.

Chahboune et al., "Application of liquid chromatography/electrospray ionization tandem mass spectrometry for the elucidation of hydroxyl radical oxidation of metsulfuron methyl and related sulfonylurea pesticide products: evidence for the triazine skeleton scission", Rapid Communications in Mass Spectrometry, vol. 29, Sep. 2015, pp. 1370-1380.

Rafqah et al., "Kinetics and mechanism of the degradation of the pesticde metsulfuron methyl induced by excitation of iron(III) aqua complexes in aqueous solutions: steady state and transient absorption spectroscopy studies", Photochem. Photobial. Sci., vol. 3, 2004, pp. 296-304.

Si et al., "Leaching and degradation of ethametsulfuron-methyl in soil", Cehmosphere, vol. 60, 2005, pp. 601-609.

Li-Feng et al., "Biodegradation of Ethametsulfuron-Methyl by Pseudomonas sp. SW4 Isolated from Contaminated Soil", Curr Microbial, vol. 55, 2007, pp. 420-426.

Non-Final Office Action received for U.S. Appl. No. 15/839,410 dated Oct. 31, 2019, 41 pages.

Final Office Action received for U.S. Appl. No. 15/839,415 dated Nov. 6, 2019, 29 pages.

Final Office Action received for U.S. Appl. No. 15/839,388 dated Dec. 5, 2019, 43 pages.

Final Office Action received for U.S. Appl. No. 15/839,397 dated Dec. 16, 2019, 31 pages.

Shen et al., "Synthesis of Highly Ordered Thermally Stable Cubic Mesostructured Zirconium Oxophosphate Templated by Tri-Headgroup Quaternary Ammonium Surfactants", Chem. Mater, vol. 15, No. 21, 2003, pp. 1046-4051.

Wang et al., "Transfection and structural properties of phytanyl substituted gemini surfactant-based vectors for gene delivery", Phys. Chem. Chem. Phys., 2013, vol. 15, pp. 20510-20516.

Non-Final Office Action received for U.S. Appl. No. 15/839,410 dated Apr. 22, 2020, 38 pages.

* cited by examiner

DISSOLVING AN AMINE MONOMER AND AN ELECTROPHILE IN A SOLVENT, THE AMINE MONOMER COMPRISING A DEGRADABLE MOLECULAR BACKBONE, AND THE DEGRADABLE MOLECULAR BACKBONE COMPRISING A TEREPHTHALAMIDE STRUCTURE — 702

FORMING A MONOMER FROM THE AMINE MONOMER AND THE ELECTROPHILE, THE MONOMER COMPRISING A SINGLE IONENE UNIT, AND THE SINGLE IONENE UNIT COMPRISING A CATION DISTRIBUTED ALONG THE DEGRADABLE MOLECULAR BACKBONE, WHEREIN THE SINGLE IONENE UNIT HAS ANTIMICROBIAL FUNCTIONALITY — 704

| Ionene Composition | SA (μg/mL) | EC (μg/mL) | PA (μg/mL) | CA (μg/mL) | Hemolysis (μg/mL) |
|---|---|---|---|---|---|
| Third Ionene Composition 316 | 8 | 63 | 500 | 16 | 500 |
| Fourth Ionene Composition 402 | >500 | 500 | >500 | >500 | >2000 |
| Fifth Ionene Composition 404 | 250 | 250 | >500 | >500 | >2000 |
| Sixth Ionene Composition 406 | >500 | >500 | >500 | >500 | >2000 |
| Seventh Ionene Composition 408 | >500 | >500 | >500 | >500 | >2000 |
| Eighth Ionene Composition 410 | 63 | 250 | >500 | 250 | >2000 |
| Ninth Ionene Composition 412 | 31 | 250 | >500 | 500 | >2000 |
| Tenth Ionene Composition 414 | 16 | 125 | >500 | 31 | >2000 |
| Twelfth Ionene Composition 418 | >500 | >500 | >500 | >500 | >2000 |
| Thirteenth Ionene Composition 420 | 500 | >500 | >500 | >500 | >2000 |
| Fourteenth Ionene Composition 422 | 4 | 16 | 125 | 63 | 1000-2000 |
| Fifteenth Ionene Composition 502 | >500 | >500 | >500 | >500 | >2000 |
| Sixteenth Ionene Composition 504 | 125 | >500 | >500 | 500 | >2000 |
| Seventeenth Ionene Composition 506 | 125 | 250 | >500 | 250 | >2000 |

```
┌─────────────────────────────────────────────────────────────┐
│ CONTACTING A PATHOGEN WITH A MONOMER, THE MONOMER           │
│ COMPRISING A SINGLE IONENE UNIT COMPRISING A CATION         │ ← 1502
│ DISTRIBUTED ALONG A MOLECULAR BACKBONE, AND A               │
│ HYDROPHOBIC FUNCTIONAL GROUP COVALENTLY BONDED TO           │
│ THE MOLECULAR BACKBONE                                      │
└─────────────────────────────────────────────────────────────┘
                              │
                              ▼
┌─────────────────────────────────────────────────────────────┐
│ ELECTROSTATICALLY DISRUPTING A MEMBRANE OF THE              │ ← 1504
│ PATHOGEN UPON CONTACTING THE PATHOGEN WITH THE              │
│ MONOMER                                                     │
└─────────────────────────────────────────────────────────────┘
```

US 10,743,537 B2

MONOMER COMPOSITIONS WITH ANTIMICROBIAL FUNCTIONALITY

BACKGROUND

The subject disclosure relates to one or more monomers with antimicrobial functionalities, and more specifically, to one or more monomers comprising one or more cations and/or hydrophobic functional groups.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, methods and/or compositions regarding ionenes with antimicrobial functionality are described.

According to an embodiment, a monomer is provided. The monomer can comprise a single ionene unit. The single ionene unit can comprise a cation distributed along a molecular backbone. Also, a hydrophobic functional group can be covalently bonded to the molecular backbone, and the single ionene unit can have antimicrobial functionality.

According to another embodiment, a monomer is provided. The monomer can comprise a single ionene unit. The single ionene unit can comprise a cation distributed along a degradable molecular backbone, which can comprise a terephthalamide structure. Further the single ionene unit can have antimicrobial functionality.

According to another embodiment, a method is provided. The method can comprise dissolving an amine monomer and an electrophile in a solvent. The electrophile can be an alkyl halide. The method can also comprise forming a monomer from the amine monomer and the electrophile. The monomer can comprise a single ionene unit. The single ionene unit can comprise a cation distributed along a molecular backbone, and the single ionene unit can have antimicrobial functionality.

According to another embodiment, a method is provided. The method can comprise dissolving an amine monomer and an electrophile in a solvent. The amine monomer can comprise a degradable molecular backbone, which can comprise a terephthalamide structure. The method can also comprise forming a monomer from the amine monomer and the electrophile. The monomer can comprise a single ionene unit. The single ionene unit can comprise a cation distributed along the degradable molecular backbone, and can have antimicrobial functionality.

According to another embodiment, a method is provided. The method can comprise contacting a pathogen with a monomer. The monomer can comprise a single ionene unit, which can comprise a cation distributed along a molecular backbone. Also, a hydrophobic functional group can be covalently bonded to the molecular backbone. Further, the single ionene unit can have antimicrobial functionality. Additionally, the contacting can electrostatically disrupt a membrane of the pathogen.

BRIEF DESCRIPTION OF THE DRAWINGS

FIG. 7 illustrates a flow diagram of an example, non-limiting method that can facilitate generating one or more ionene units in accordance with one or more embodiments described herein.

FIG. 10 illustrates a diagram of an example, non-limiting chart that can depict antimicrobial functionality of various ionene compositions in accordance with one or more embodiments described herein.

FIG. 15 illustrates a flow diagram of an example, non-limiting method that can facilitate killing of a pathogen with one or more ionene units in accordance with one or more embodiments described herein.

DETAILED DESCRIPTION

Figure 1A:
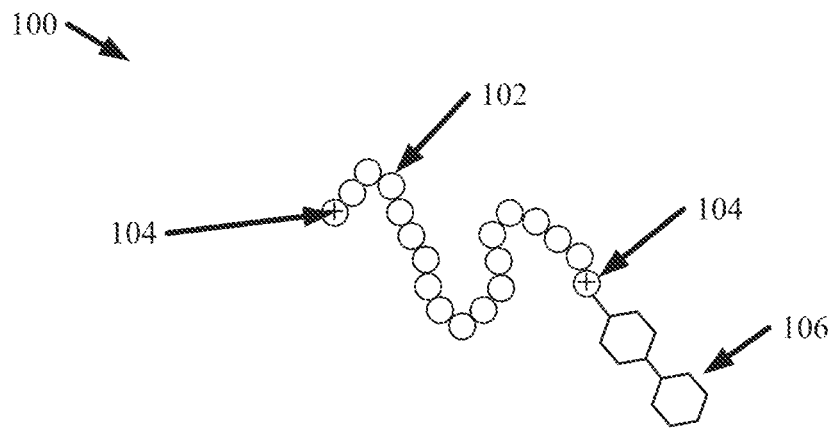
FIG. 1A illustrates a diagram of an example, non-limiting ionene unit in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

The discovery and refinement of antibiotics was one of the crowning achievements in the $20^{th}$ century that revolutionized healthcare treatment. For example, antibiotics such as penicillin, ciprofloxacin and, doxycycline can achieve microbial selectivity through targeting and disruption of a specific prokaryotic metabolism, while concurrently, remaining benign toward eukaryotic cells to afford high selectivity. If properly dosed, they could eradicate infection. Unfortunately, this therapeutic specificity of antibiotics also leads to their undoing as under-dosing (incomplete kill) allows for minor mutative changes that mitigate the effect of the antibiotic leading to resistance development. Consequently, nosocomial infections, caused by medication-resistant microbes such as methicillin-resistant *Staphylococcus aureus* (MRSA), multi-medication-resistant *Pseudomonas aeruginosa* and vancomycin-resistant Enterococci (VRE) have become more prevalent. An added complexity is the pervasive use of antimicrobial agents in self-care products, sanitizers and hospital cleaners etc, including anilide, bisphenols, biguanides and quaternary ammonium compounds, where a major concern is the development of cross- and co-resistance with clinically used antibiotics, especially in a hospital setting. Another unfortunate feature with triclosan, for example, is its cumulative and persistent effects in the skin. Moreover, biofilms have been associated with numerous nosocomial infections and implant failure, yet the eradication of biofilms is an unmet challenge to this date. Since antibiotics are not able to penetrate through extracellular polymeric substance that encapsulates bacteria in the biofilm, further complexities exist that lead to the development of medication resistance.

However, polymers having a cationic charge can provide electrostatic disruption of the bacterial membrane interaction. Furthermore, cationic polymers are readily made amphiphilic with addition of hydrophobic regions permitting both membrane association and integration/lysis. The amphiphilic balance has shown to play an important effect not only in the antimicrobial properties but also in the hemolytic activity. Many of these antimicrobial polymers show relatively low selectivity as defined by the relative toxicity to mammalian cells or hemolysis relative to pathogens.

As used herein, the term "ionene" can refer to a polymer unit, a copolymer unit, and/or a monomer unit that can comprise a nitrogen cation and/or a phosphorus cation distributed along, and/or located within, a molecular backbone, thereby providing a positive charge. Example nitrogen cations include, but are not limited to: quaternary ammonium cations, protonated secondary amine cations, protonated tertiary amine cations, and/or imidazolium cations. Example, phosphorus cations include, but are not limited to: quaternary phosphonium cations, protonated secondary phosphine cations, and protonated tertiary phosphine cations. As used herein, the term "molecular backbone" can refer to a central chain of covalently bonded atoms that form the primary structure of a molecule. In various embodiments described herein, side chains can be formed by bonding one or more functional groups to a molecular backbone. As used herein, the term "polyionene" can refer to a polymer that can comprise a plurality of ionenes. For example, a polyionene can comprise a repeating ionene.

FIG. 1A illustrates a diagram of an example, non-limiting ionene unit 100 in accordance with one or more embodiments described herein. The ionene unit 100 can comprise a molecular backbone 102, one or more cations 104, and/or one or more hydrophobic functional groups 106. In various embodiments, an ionene and/or a polyionene described herein can comprise the ionene unit 100. For example, a polyionene described herein can comprise a plurality of ionenes bonded together, wherein the bonded ionenes can have a composition exemplified by ionene unit 100.

Figure 1B:
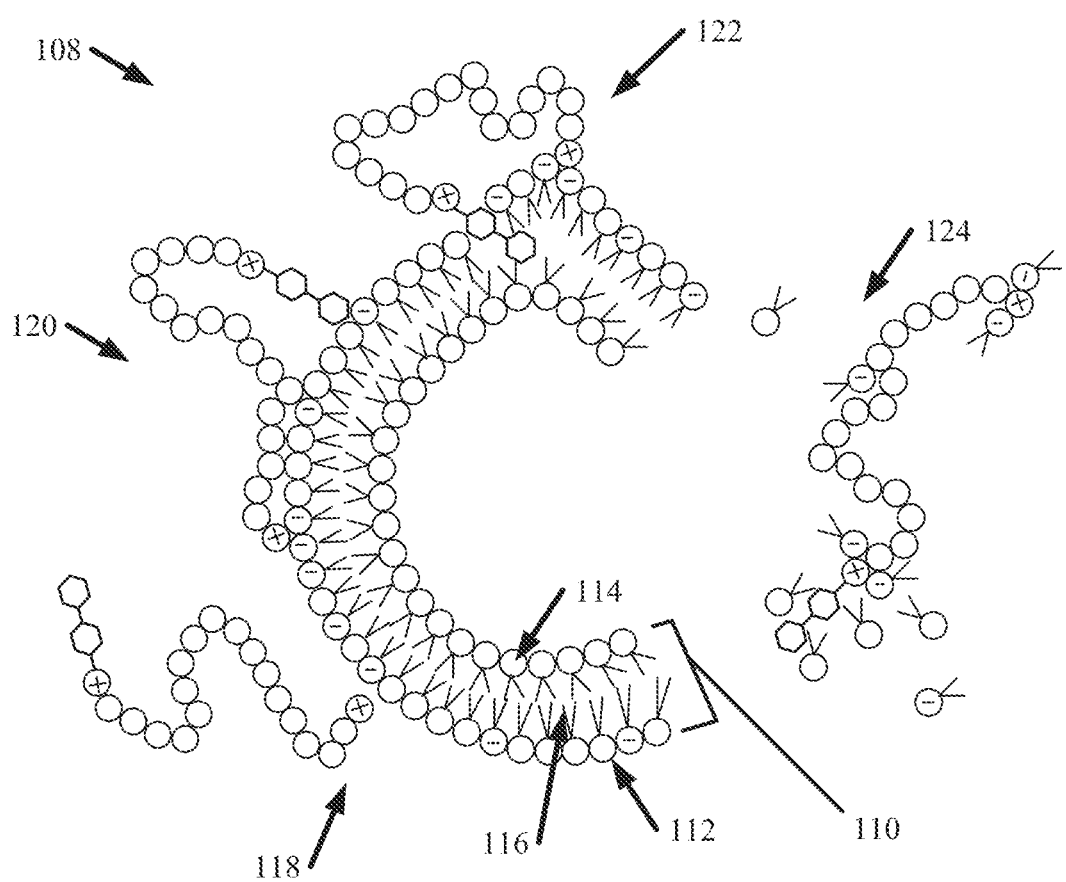
FIG. 1B illustrates a diagram of an example, non-limiting lysis process that can be performed by one or more ionene units in accordance with one or more embodiments described herein.

The molecular backbone 102 can comprise a plurality of covalently bonded atoms (illustrated as circles in FIGS. 1A and 1B). The atoms can be bonded in any desirable formation, including, but not limited to: chain formations, ring formations, and/or a combination thereof. The molecular backbone 102 can comprise one or more chemical structures including, but not limited to: alkyl structures, aryl structures, alkenyl structures, aldehyde structures, ester structures, carboxyl structures, carbonyl structures, amine structures, amide structures, phosphide structures, phosphine structures, a combination thereof, and/or the like. One of ordinary skill in the art will recognize that the number of atoms that can comprise the molecular backbone can vary depending of the desired function of the ionene unit 100. For example, while nineteen atoms are illustrated in FIG. 1A, a molecular backbone 102 that can comprise dozens, hundreds, and/or thousands of atoms is also envisaged.

Located within the molecular backbone 102 are one or more cations 104. As described above, the one or more cations 104 can comprise nitrogen cations and/or phosphorous cations. The cations 104 can be distributed along the molecular backbone 102, covalently bonded to other atoms within the molecular backbone 102. In various embodiments, the one or more cations 104 can comprise at least a portion of the molecular backbone 102. One of ordinary skill in the art will recognize that the number of a cations 104 that can comprise the ionene unit 100 can vary depending of the desired function of the ionene unit 100. For example, while two cations 104 are illustrated in FIG. 1A, an ionene unit 100 that can comprise dozens, hundreds, and/or thousands of cations 104 is also envisaged. Further, while FIG. 1A illustrates a plurality of cations 104 evenly spaced apart, other configurations wherein the cations 104 are not evenly spaced apart are also envisaged. Also, the one or more cations 104 can be located at respective ends of the molecular backbone 102 and/or at intermediate portions of the molecular backbone 102, between two or more ends of the molecular backbone 102. The one or more cations 104 can provide a positive charge to one or more locations of the ionene unit 100.

The one or more hydrophobic functional groups 106 can be bonded to the molecular backbone 102 to form a side chain. The one or more of the hydrophobic functional groups 106 can be attached to the molecular backbone 102 via bonding with a cation 104. Additionally, one or more hydrophobic functional groups 106 can be bonded to an electrically neutral atom of the molecular backbone 102. The ionene unit 100 can comprise one or more hydrophobic functional groups 106 bonded to: one or more ends of the molecular backbone 102, all ends of the molecular backbone 102, an intermediate portion (e.g., a portion between two ends) of the molecular backbone 102, and/or a combination thereof.

While a biphenyl group is illustrated in FIG. 1A as the hydrophobic functional group 106, other functional groups that are hydrophobic are also envisaged. Example, hydrophobic functional groups 106 can include, but are not limited to: alkyl structures, aryl structures, alkenyl structures, ester structures, carboxyl structures, carbonyl structures, carbonate structures, alcohol structures, a combination thereof, and/or the like. In various embodiments, the one or more hydrophobic functional groups 106 can comprise the same structure. In other embodiments, one or more of the hydrophobic functional groups 106 can comprise a first structure and one or more other hydrophobic functional groups 106 can comprise another structure.

FIG. 1B illustrates a diagram of an example, non-limiting lysis process 108 that can be facilitated by the ionene unit 100 in accordance with one or more embodiments described herein. Repetitive description of like elements employed in other embodiments described herein is omitted for sake of brevity. The lysis process 108 can comprise a plurality of stages, which can collectively comprise an attack mechanism that can be performed by the ionene unit 100 against a pathogen cell. Example pathogen cells can include, but are not limited to: Gram-positive bacteria cells, Gram-negative bacteria cells, fungi cells, and/or yeast cells.

The target pathogen cell can comprise a membrane having a phospholipid bilayer 110. In various embodiments, the membrane can be an extracellular matrix. The phospholipid bilayer 110 can comprise a plurality of membrane molecules 112 covalently bonded together, and the membrane molecules 112 can comprise a hydrophilic head 114 and one or more hydrophobic tails 116. Further, one or more of the plurality of membrane molecules 112 can be negatively charged (as illustrated in FIG. 1B with a "−" symbol).

At 118, electrostatic interaction can occur between the positively charged cations 104 of the ionene unit 100 and one or more negatively charged membrane molecules 112. For example, the negative charge of one or more membrane molecules 112 can attract the ionene unit 100 towards the membrane (e.g., the phospholipid bilayer 110). Also, the electrostatic interaction can electrostatically disrupt the integrity of the membrane (e.g., phospholipid bilayer 110). Once the ionene unit 100 has been attracted to the membrane (e.g., phospholipid bilayer 110), hydrophobic membrane integration can occur at 120. For example, at 120 one or more hydrophobic functional groups 106 of the ionene unit 100 can begin to integrate themselves into the phospholipid bilayer 110. While the positively charged portions of the ionene unit 100 are attracted, and electrostatically disrupting, one or more negatively charged membrane molecules 112 (e.g., one or more hydrophilic heads 114), the one or more hydrophobic functional groups 106 can insert themselves between the hydrophilic heads 114 to enter a hydrophobic region created by the plurality of hydrophobic tails 116.

As a result of the mechanisms occurring at 118 and/or 120, destabilization of the membrane (e.g., the phospholipid bilayer 110) can occur at 122. For example, the one or more hydrophobic functional groups 106 can serve to cleave one or more negatively charged membrane molecules 112 from adjacent membrane molecules 112, and the positively charged ionene unit 100 can move the cleaved membrane segment (e.g., that can comprise one or more negatively charged membrane molecules 112 and/or one or more neutral membrane molecules 112 constituting a layer of the phospholipid bilayer 110) away from adjacent segments of the membrane (e.g., adjacent segments of the phospholipid bilayer 110). As cleaved segments of the membrane (e.g., the phospholipid bilayer 110) are pulled away, they can fully detach from other membrane molecules 112 at 124, thereby forming gaps in the membrane (e.g., the phospholipid bilayer 110). The formed gaps can contribute to lysis of the subject pathogen cell. In various embodiments, a plurality of ionene units 100 can perform the lysis process 108 on a cell simultaneously. Furthermore, the ionene units 100 participating in a lysis process 108 need not perform the same stages of the attack mechanism at the same time.

Figure 2:
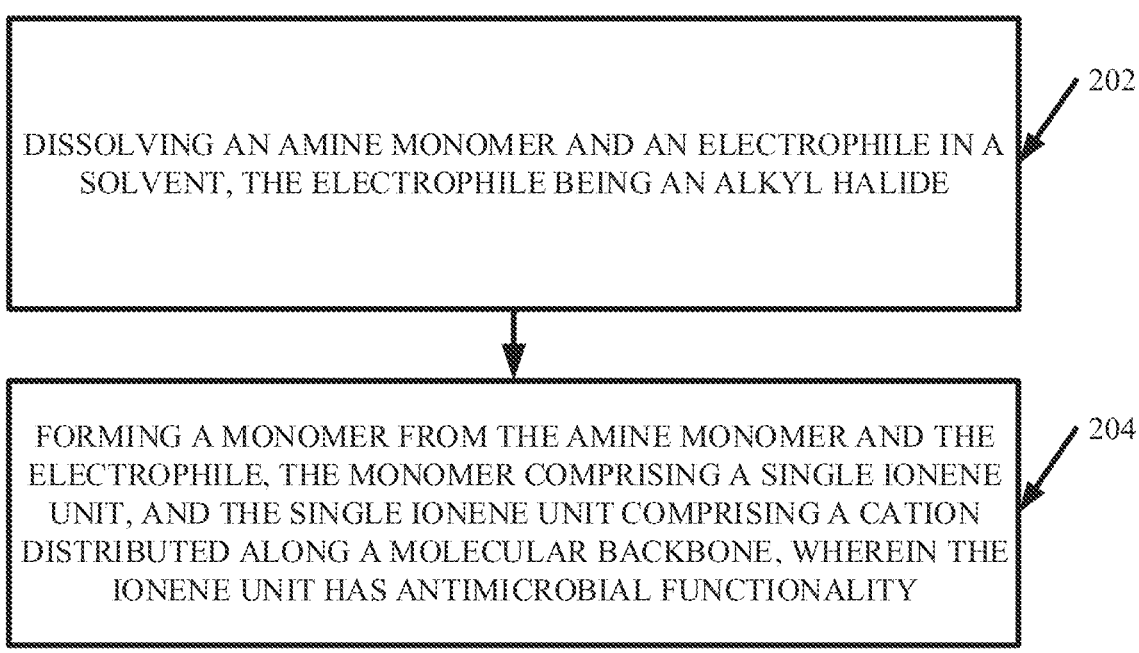
FIG. 2 illustrates a flow diagram of an example, non-limiting method that can facilitate generating one or more ionene compositions in accordance with one or more embodiments described herein.

FIG. 2 illustrates a flow diagram of an example, non-limiting method 200 that can facilitate generation of one or more ionene units 100 (e.g., that can be characterized by FIGS. 1A and/or 1B) in accordance with one or more embodiments described herein. Repetitive description of like elements employed in other embodiments described herein is omitted for sake of brevity. Method 200 can be performed with commercially available amine monomers and/or commercially available electrophiles to generate one or more ionene units 100. The ionene units 100 formed by method 200 can comprise one or more monomers.

At 202, the method 200 can comprise dissolving one or more amine monomers and one or more electrophiles in a solvent. The one or more amine monomers can comprise one or more amino groups. Example amino groups that can comprise the one or more amine monomers can include, but are not limited to: primary amino groups, secondary amino groups, tertiary amino groups, heterocyclic groups (e.g., imidazole groups and/or pyridine groups), a combination thereof, and/or the like. For example, the one or more amine monomers can comprise a tertiary amino group. Also, wherein the one or more amine monomers comprise a plurality of amino groups, a first amino group of the subject amine monomer can have the same or a different structure than a second amino group of the subject amine monomer. For example, the one or more amine monomers can comprise two or more tertiary amino groups. Additionally, the one or more amine monomers can comprise alkyl and/or aryl structures. Moreover, the one or more amine monomers can comprise one or more functional groups (e.g., hydroxyl groups). Example amine monomers can include, but are not limited to: 1-butylimidazole; N-methyldiethanolamine; bis [2-(N,N-dimethylamino)ethyl] ether; N,N,N',N'-tetramethyl-p-phenylenediamine; N,N-dimethylbenzylamine; diethanolamine derivative compounds; a combination thereof; and/or the like.

The one or more electrophiles can comprise alkyl halides (e.g., dialkyl halides). For example, the one or more electrophiles can comprise bromide and/or chloride. Example, electrophiles can include, but are not limited to: p-xylylene dichloride; 4,4'-bis(chloromethyl)biphenyl; 1,4-bis(bromomethyl)benzene; 4,4'-bis(bromomethyl)biphenyl; 1,4-bis (iodomethyl)benzene; 1,6-dibromohexane; 1,8-dibromooctane; 1,12-dibromododecane; 1,6-dichlorohexane; 1,8-dichlorooctane; benzyl bromide; 3-chloro-1-propanol; 1-bromohexane; 2-(2-chloroethoxy)ethanol; 3-chloro-1,2-propanediol; 1-bromooctane; 1-bromododecane; benzyl chloride; a combination thereof; and/or the like.

The solvent can be an organic solvent. Additionally, the solvent can be an a protic and/or aprotic solvent, and/or an alcohol. Example solvents can include but are not limited to: dimethyl formamide (DMF), methanol, tetrahydrofuran (THF), dichloromethane (DCM), a combination thereof, and/or the like. To facilitate the dissolving, the method 200 can further comprise stirring one or more amine monomers, the one or more electrophiles, and/or the solvent at a temperature greater than or equal to 15 degrees Celsius (° C.) and less than or equal to 150° C. for a period of time greater than or equal to 8 hours and less than or equal to 72 hours (e.g., greater than or equal to 12 hours and less than or equal to 24 hours).

At 204, the method 200 can comprise forming one or more monomers from the one or more amine monomers and/or the one or more electrophiles, and each monomer can comprise a single ionene unit 100. The one or more electrophiles can be covalently bonded to one or more amino groups of the one or more amine monomers. For example, the forming at 204 can comprise subjecting one or more amino groups of the one or more amine monomers to an alkylation and/or quaternization with the one or more electrophiles, whereby the alkylation and/or quaternization can ionize the one or more amino groups. Thus, the forming at 204 can conduct a polymer-forming reaction (e.g., formation of the ionene unit 100) and an installation of charge (e.g., forming a cation 104) simultaneously.

The one or more single ionene units 100 comprising the one or more monomers can comprise one or more cations 104 (e.g., formed by an ionization of one or more amino groups at 204) distributed along a molecular backbone 102. The one or more cations 104 can comprise protonated secondary amine cations, protonated tertiary amine cations, quaternary ammonium cations, imidazolium cations, and/or a combination thereof. Additionally, the one or more single ionene units 100 comprising the one or more monomers can comprise one or more hydrophobic functional groups 106 covalently bonded to the molecular backbone 102 (e.g., via the one or more cations 104). For example, the one or more hydrophobic functional groups 106 can be derived from the one or more electrophiles and/or formed by the alkylation and/or quaternization at 204. The one or more single ionene units 100, and thereby the one or more monomers, formed at 204 can have antimicrobial functionality.

Figure 3:
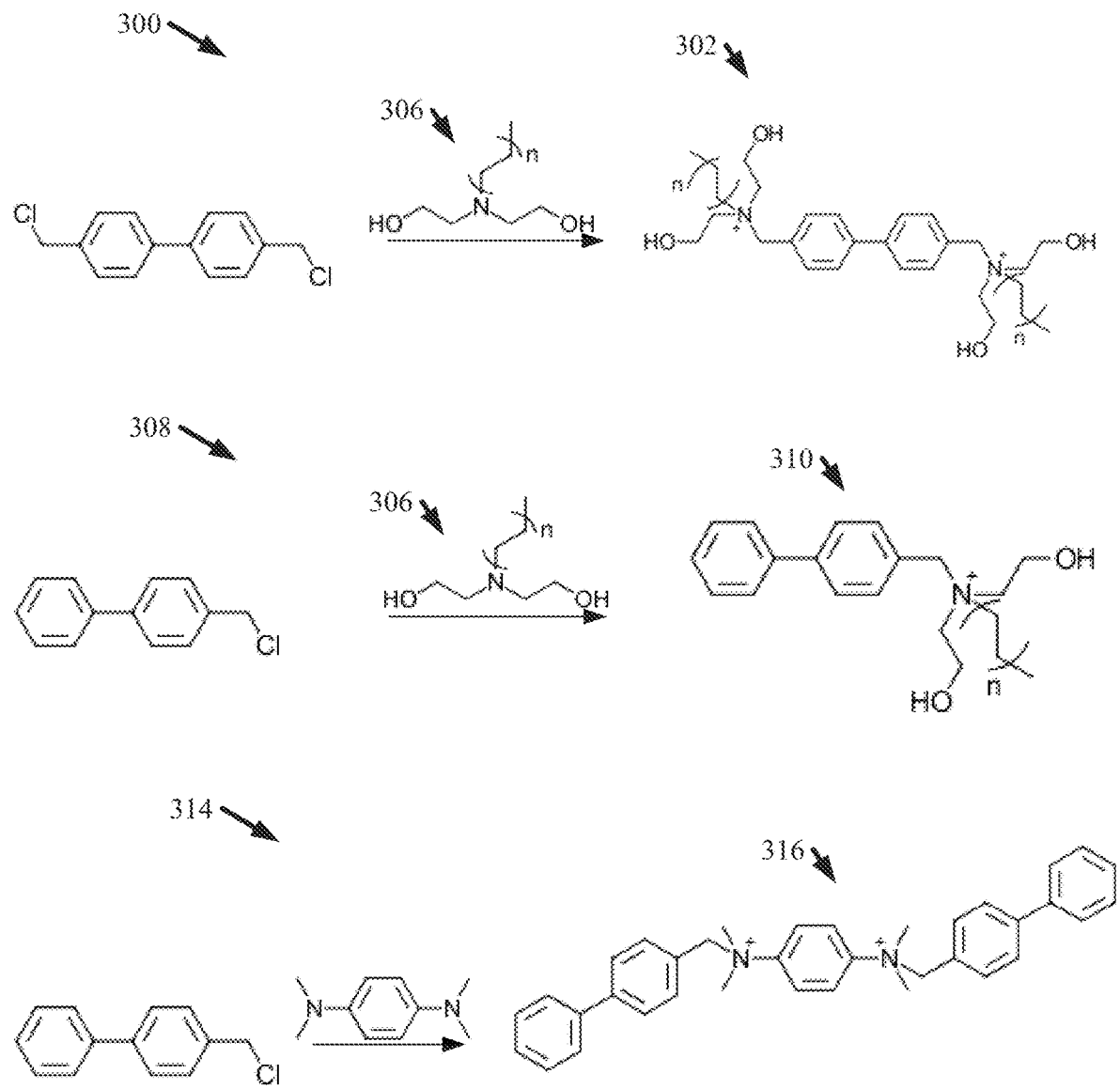
FIG. 3 illustrates a diagram of example, non-limiting compound-forming schemes that can facilitate generating one or more ionene compositions in accordance with one or more embodiments described herein.

FIG. 3 illustrates a diagram of example, non-limiting compound-forming schemes that can facilitate generation of one or more ionene compositions (e.g., that can be characterized by FIGS. 1A and 1B and/or generated in accordance with method 200) in accordance with one or more embodiments described herein. Repetitive description of like elements employed in other embodiments described herein is omitted for sake of brevity. The compound-forming schemes shown in FIG. 3 can be performed with commercially available amine monomers and/or commercially available electrophiles to generate one or more ionene units 100. The ionene units 100 formed by generated by the compound-forming schemes of FIG. 3 can comprise one or more monomers. Also, the "n" in FIG. 3 can represent an integer greater than or equal to one and less than or equal to one thousand (e.g., an integer greater than or equal to one and less than or equal to one hundred). While one or more particular amine monomers and/or electrophiles are depicted; additional embodiments of the compound-forming schemes shown in FIG. 3 are also envisaged. For example, the principal mechanisms of the compound-forming schemes shown in FIG. 3 can be applied to any amine monomer and/or electrophile in accordance with the various features described herein (e.g., with reference to FIGS. 1A-1B and/or method 200).

As shown in FIG. 3, the scheme 300 can depict forming an ionene composition (e.g., first ionene composition 302) from a dialkyl halide (e.g., 4,4'-bis(chloromethyl)-1,1'-biphenyl) and a plurality of amine monomers (e.g., first amine monomer 306). For example, the dialkyl halide (e.g., 4,4'-bis(chloromethyl)-1,1'-biphenyl) can be dissolved with the plurality of amine monomers (e.g., first amine monomer 306) in solvent (e.g., DMF). The dialkyl halide (e.g., 4,4'-bis(chloromethyl)-1,1'-biphenyl), the plurality of amine monomers (e.g., first amine monomer 306), and the solvent can be stirred at a temperature greater than or equal to 15° C. and less than or equal to 150° C. (e.g., room temperature ("RT")) for a period of time greater than or equal to 8 hours and less than or equal to 72 hours (e.g., greater than or equal to 12 hours and less than or equal to 24 hours).

The scheme 300 can covalently bond the plurality of amine monomers (e.g., first amine monomers 306) to the electrophile (e.g., 4,4'-bis(chloromethyl)-1,1'-biphenyl) through one or more amino groups (e.g., tertiary amino groups) of the plurality of amine monomers (e.g., first amine monomers 306). For example, the scheme 300 can comprise an alkylation of the one or more amino groups (e.g., tertiary amino groups) with the electrophile (e.g., 4,4'-bis(chloromethyl)-1,1'-biphenyl) to form the ionene composition (e.g., first ionene composition 302) comprising a plurality of cations 104 (e.g., quaternary ammonium cations). Further, the ionene composition (e.g., first ionene composition 302) can comprise one or more hydrophobic functional groups 106 derived from the electrophile (e.g., 4,4'-bis(chloromethyl)-1,1'-biphenyl) as a result of the alkylation. Thus, the ionene compositions (e.g., first ionene composition 302) that can be generated by scheme 300 can comprise the various features described in reference to FIGS. 1A-1B and/or can be generated in accordance with the various features of method 200.

As shown in FIG. 3, the scheme 308 can depict forming an ionene composition (e.g., second ionene composition 310) from an alkyl halide (e.g., 4-(chloromethyl)biphenyl) and an amine monomer (e.g., first amine monomer 306). For example, the alkyl halide (e.g., 4-(chloromethyl)biphenyl) can be dissolved with the amine monomer (e.g., first amine monomer 306) in solvent (e.g., DMF). The alkyl halide (e.g., 4-(chloromethyl)biphenyl), the amine monomer (e.g., first amine monomer 306), and the solvent can be stirred at a temperature greater than or equal to 15° C. and less than or equal to 150° C. (e.g., room temperature ("RT")) for a period of time greater than or equal to 8 hours and less than or equal to 72 hours (e.g., greater than or equal to 12 hours and less than or equal to 24 hours).

The scheme 308 can covalently bond the amine monomer (e.g., first amine monomers 306) to the electrophile (e.g., 4-(chloromethyl)biphenyl) through one or more amino groups (e.g., tertiary amino groups) of the amine monomer (e.g., first amine monomers 306). For example, the scheme 308 can comprise an alkylation of the one or more amino groups (e.g., tertiary amino groups) with the electrophile (e.g., 4-(chloromethyl)biphenyl) to form the ionene composition (e.g., second ionene composition 310) comprising a cation 104 (e.g., a quaternary ammonium cation). Further, the ionene composition (e.g., second ionene composition 310) can comprise one or more hydrophobic functional groups 106 derived from the electrophile (e.g., 4-(chloromethyl)biphenyl) as a result of the alkylation. Thus, the ionene compositions (e.g., second ionene composition 310) that can be generated by scheme 308 can comprise the various features described in reference to FIGS. 1A-1B and/or can be generated in accordance with the various features of method 200.

As shown in FIG. 3, the scheme 314 can depict forming an ionene composition (e.g., third ionene composition 316) from a plurality of alkyl halides (e.g., 4-(chloromethyl) biphenyl) and a diamine monomer (e.g., N,N,N',N'-tetramethyl-p-phenylenediamine). For example, the plurality of alkyl halides (e.g., 4-(chloromethyl)biphenyl) can be dissolved with the diamine monomer (e.g., N,N,N',N'-tetramethyl-p-phenylenediamine) in solvent (e.g., DMF). The plurality of alkyl halides (e.g., 4-(chloromethyl)biphenyl), the diamine monomer (e.g., N,N,N',N'-tetramethyl-p-phenylenediamine), and the solvent can be stirred at a temperature greater than or equal to 15° C. and less than or equal to 150° C. (e.g., room temperature ("RT")) for a period of time greater than or equal to 8 hours and less than or equal to 72 hours (e.g., greater than or equal to 12 hours and less than or equal to 24 hours).

The scheme 314 can covalently bond the plurality of alkyl halides (e.g., 4-(chloromethyl)biphenyl) to the diamine monomer (e.g., N,N,N',N'-tetramethyl-p-phenylenediamine) through one or more amino groups (e.g., tertiary amino groups) of the diamine monomer (e.g., N,N,N',N'-tetramethyl-p-phenylenediamine). For example, the scheme 314 can comprise an alkylation of the one or more amino groups (e.g., tertiary amino groups) with the plurality of electrophiles (e.g., 4-(chloromethyl)biphenyl) to form the ionene composition (e.g., third ionene composition 316) comprising a plurality of cations 104 (e.g., quaternary ammonium cations). Further, the ionene composition (e.g., third ionene composition 316) can comprise one or more hydrophobic functional groups 106 derived from the plurality of electrophiles (e.g., 4-(chloromethyl)biphenyl) as a result of the alkylation. Thus, the ionene compositions (e.g., third ionene composition 316) that can be generated by scheme 314 can comprise the various features described in reference to FIGS. 1A-1B and/or can be generated in accordance with the various features of method 200.

Figure 4:
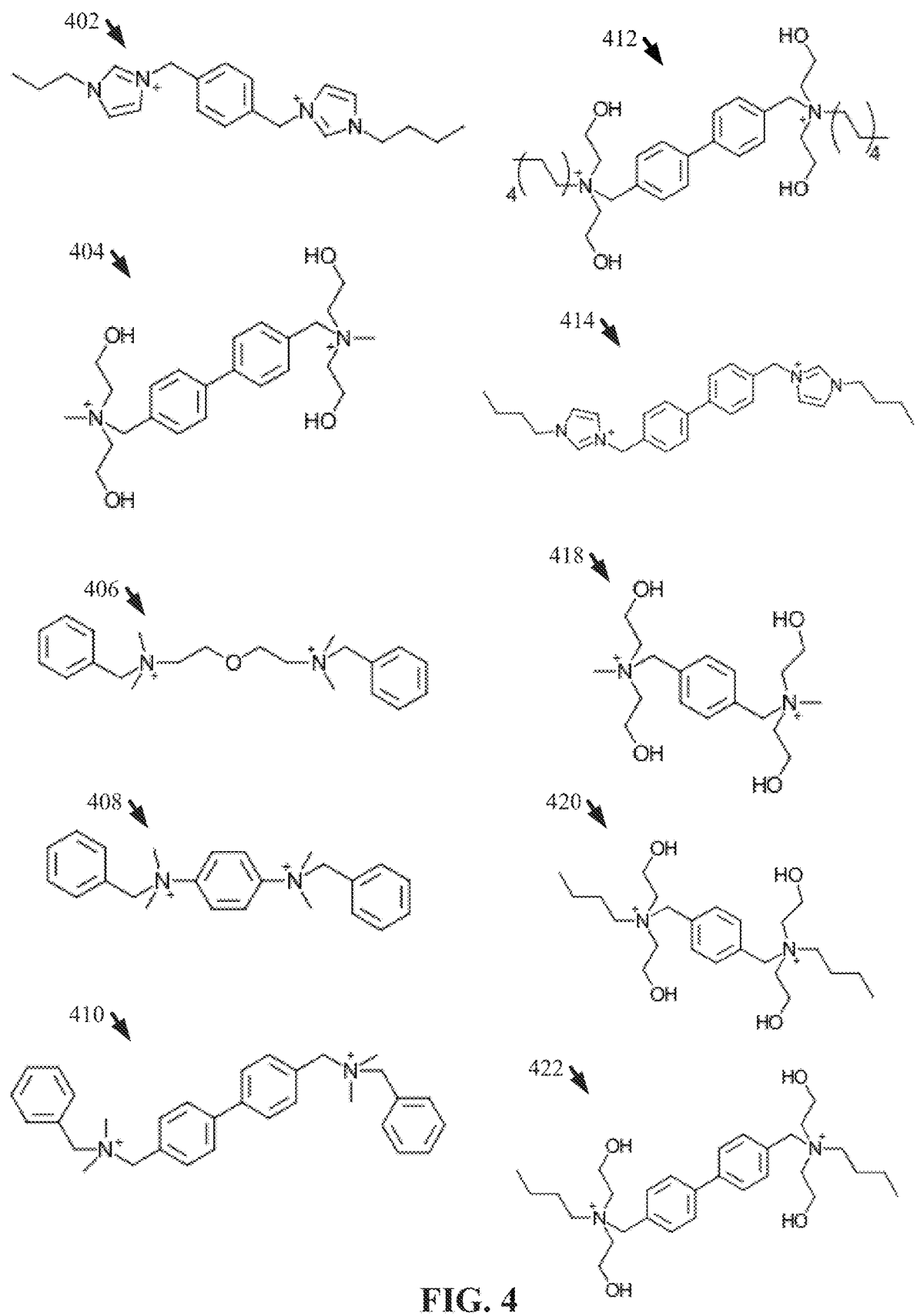
FIG. 4 illustrates a diagram of example, non-limiting ionene compositions in accordance with one or more embodiments described herein.

FIG. 4 illustrates a diagram of example, non-limiting ionene compositions that can comprise a single ionene unit 100, which can comprise the various features described in regards to FIGS. 1A-1B and/or can be generated in accordance with the various features of method 200 and/or the compound-forming schemes shown in FIG. 3. Repetitive description of like elements employed in other embodiments described herein is omitted for sake of brevity. The ionene compositions shown in FIG. 4 can be monomers and can have antimicrobial functionality.

For example, FIG. 4 can show a fourth ionene composition 402, a fifth ionene composition 404, a sixth ionene composition 406, a seventh ionene composition 408, an eighth ionene composition 410, a ninth ionene composition 412, a tenth ionene composition 414, a twelfth ionene composition 418, a thirteenth ionene composition 420, and/or a fourteenth ionene composition 422. Each of the ionene compositions shown in FIG. 4 can be generated in accordance with the various features of method 200. Further, each of the ionene compositions shown in FIG. 4 can be generated in accordance with the principal mechanisms shown in the plurality of compound-forming schemes of FIG. 3.

Figure 5:
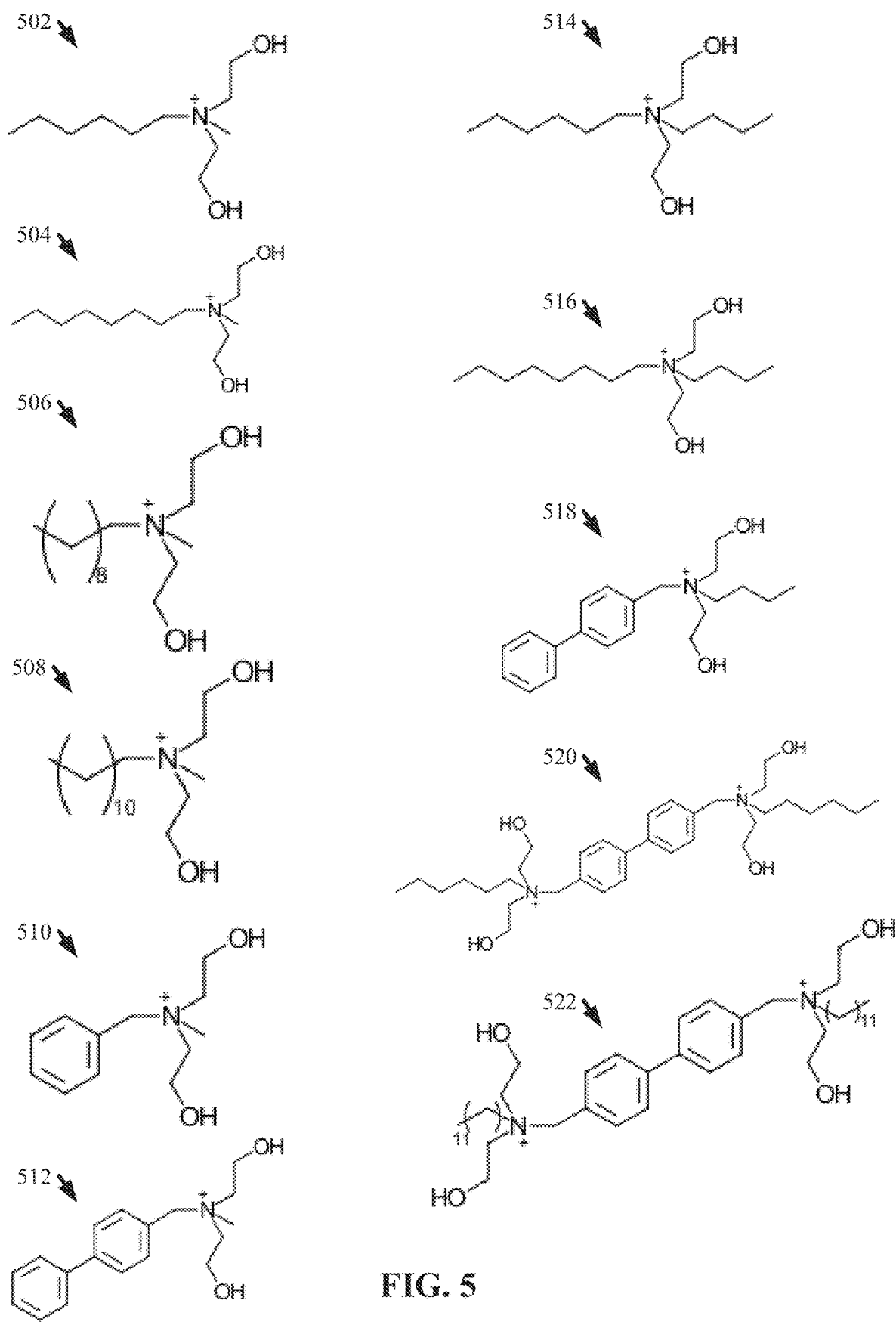
FIG. 5 illustrates another diagram of example, non-limiting ionene compositions in accordance with one or more embodiments described herein.

FIG. 5 illustrates another diagram of example, non-limiting ionene compositions that can comprise a single ionene unit 100, which can comprise the various features described in regards to FIGS. 1A-1B and/or can be generated in accordance with the various features of method 200 and/or the compound-forming schemes shown in FIG. 3. Repetitive description of like elements employed in other embodiments described herein is omitted for sake of brevity. The ionene compositions shown in FIG. 5 can be monomers and can have antimicrobial functionality.

For example, FIG. 5 can show a fifteenth ionene composition 502, a sixteenth ionene composition 504, a seventeenth ionene composition 506, an eighteenth ionene composition 508, a nineteenth ionene composition 510, a twentieth ionene composition 512, a twenty-first ionene composition 514, a twenty-second ionene composition 516, a twenty-third ionene composition 518, a twenty-fourth ionene composition 520, and/or a twenty-fifth ionene composition 522. Each of the ionene compositions shown in FIG. 5 can be generated in accordance with the various features of method 200. Further, each of the ionene compositions shown in FIG. 5 can be generated in accordance with the principal mechanisms shown in the plurality of compound-forming schemes of FIG. 3.

Figure 6:
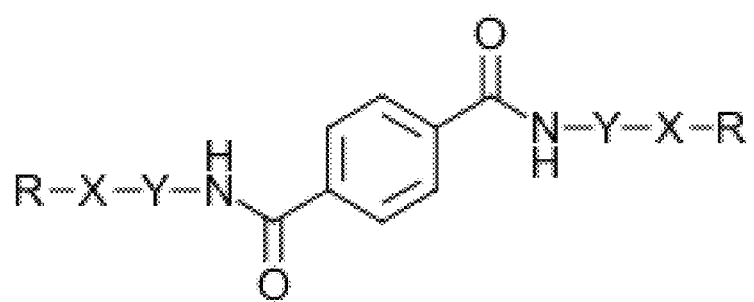
FIG. 6 illustrates a diagram of an example, non-limiting chemical formula that can characterize one or more ionene units in accordance with one or more embodiments described herein.

FIG. 6 illustrates a diagram of an example, non-limiting chemical formula 600 that can characterize the structure of an ionene unit 100 in accordance with one or more embodiments described herein. Repetitive description of like elements employed in other embodiments described herein is omitted for sake of brevity. In various embodiments, one or more ionene units 100 characterized by chemical formula 600 can comprise a monomer composition.

As shown in FIG. 6, one or more ionene units 100 characterized by chemical formula 600 can comprise a degradable molecular backbone 102. Further, the degradable molecular backbone 102 can comprise one or more terephthalamide structures. In various embodiments, the one or more ionene units 100 characterized by chemical formula 600 can be derived from polyethylene terephthalate (PET), wherein the one or more terephthalamide structures can be derived from the PET. However, one or more embodiments of chemical formula 600 can comprise a terephthalamide structure derived from one or more molecules other than PET.

The "X" in FIG. 6 can represent the one or more cations 104. For example, "X" can represent one or more cations 104 selected from a group that can include, but is not limited to: one or more nitrogen cations, one or more phosphorus cations, and/or a combination thereof. For instance, "X" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. In another instance, "X" can represent one or more phosphorus cations selected from a group that can include, but is not limited to: one or more protonated secondary phosphine cations, one or more protonated tertiary phosphine cations, one or more quaternary phosphonium cations, and/or a combination thereof.

The one or more cations 104 (e.g., represented by "X" in chemical formula 600) can be covalently bonded to one or more linkage groups to form, at least a portion, of the degradable molecular backbone 102. The one or more linkage groups can link the one or more cations 104 to the one or more terephthalamide structures, thereby comprising the molecular backbone 102. The "Y" in FIG. 6 can represent the one or more linkage groups. The one or more linkage groups can comprise any structure in compliance with the various features of the molecular backbone 102 described herein. For example, the one or more linkage groups can have any desirable formation, including, but not limited to: chain formations, ring formations, and/or a combination thereof. The one or more linkage groups can comprise one or more chemical structures including, but not limited to: alkyl structures, aryl structures, alkenyl structures, aldehyde structures, ester structures, carboxyl structures, carbonyl structures, a combination thereof, and/or the like. For instance, "Y" can represent one or more linkage groups that can comprise an alkyl chain having greater than or equal to two carbon atoms and less than or equal to 15 carbon atoms.

As shown in FIG. 6, in various embodiments, a one or more ionene units 100 characterized by chemical formula 600 can comprise cations 104 (e.g., represented by "X") at a plurality of locations along the molecular backbone 102. For example, cations 104 can be located at either end of the molecular backbone 102 (e.g., as illustrated in FIG. 6). However, in one or more embodiments of chemical formula 600, the molecular backbone 102 can comprise less or more cations 104 than the two illustrated in FIG. 6.

Further, the "R" shown in FIG. 6 can represent the one or more hydrophobic functional groups 106 in accordance with the various embodiments described herein. For example, the one or more hydrophobic functional groups 106 can comprise one or more alkyl groups and/or one or more aryl groups. For instance, the hydrophobic functional group 106 can be derived from an alkyl halide. The one or more hydrophobic functional groups 106 (e.g., represented by "R" in FIG. 6) can be covalently bonded to one or more of the cations 104 (e.g., represented by "X" in FIG. 6) and/or the molecular backbone 102, which can comprise the one or more cations 104 (e.g., represented by "X" in FIG. 6), one or more linkage groups (e.g., represented by "Y" in FIG. 6), and/or one or more terephthalamide structures.

FIG. 7 illustrates another flow diagram of an example, non-limiting method 700 that can facilitate generating one or more ionene units 100, which can be characterized by chemical formula 600. Repetitive description of like elements employed in other embodiments described herein is omitted for sake of brevity. The one or more ionene units 100 generated by method 700 can comprise monomer compositions and/or can have antimicrobial functionality.

At 702, the method 700 can comprise dissolving one or more amine monomers with one or more electrophiles in a solvent. The one or more amine monomers can comprise a degradable molecular backbone 102, which can comprise one or more terephthalamide structures. Additionally, the amine monomer can comprise one or more amino groups. For example, the one or more amine monomers can be tetra-amines. Example amino groups that can comprise the one or more amine monomers can include, but are not limited to: primary amino groups, secondary amino groups, tertiary amino groups, heterocyclic groups (e.g., imidazole groups and/or pyridine groups), a combination thereof, and/or the like. Further, wherein the one or more amine monomers comprise a plurality of amino groups, a first amino group of a subject amine monomer can have the same or a different structure than a second amino group of the subject amine monomer.

The one or more electrophiles can comprise, for example, one or more alkyl halides (e.g., dialkyl halides). For instance, the one or more electrophiles can comprise chloride and/or bromide. Example electrophiles can include, but are not are not limited to: benzyl chloride; 3-chloro-1-propanol; 1-bromohexane; 2-(2-chloroethoxy)ethanol; 3-chloro-1,2-propanediol; 1-bromooctane; 1-bromododecane; 4-(chloromethyl)biphenyl; 1-bromodecane; a combination thereof; and/or the like.

The solvent can be an organic solvent. Additionally, the solvent can be an a protic and/or aprotic solvent, and/or an alcohol. Example solvents can include but are not limited to: dimethyl formamide (DMF), methanol, tetrahydrofuran (THF), dichloromethane (DCM), a combination thereof, and/or the like. To facilitate the dissolving, the method 200 can further comprise stirring one or more amine monomers, the one or more electrophiles, and/or the solvent at a temperature greater than or equal to 15° C. and less than or equal to 150° C. for a period of time greater than or equal to 8 hours and less than or equal to 72 hours (e.g., greater than or equal to 12 hours and less than or equal to 24 hours).

In one or more embodiments, the one or more amine monomers can be prepared through an aminolysis of PET. For example, PET can be depolymerized with one or more aminolysis reagents. The one or more aminolysis reagents can be diamines. A first amino group of the diamines can include, but are not limited to, a primary amino group and a secondary amino group. Also, a second amino group of the diamines can include, but are not limited to: a primary amino group, a secondary amino group, a tertiary amino group, and/or an imidazole group. For example, in one or more embodiments the secondary amino group is a tertiary amino group and/or an imidazole group.

Scheme 1, presented below, demonstrates three exemplary, non-liming degradable amine monomers that can be prepared through aminolysis of PET.

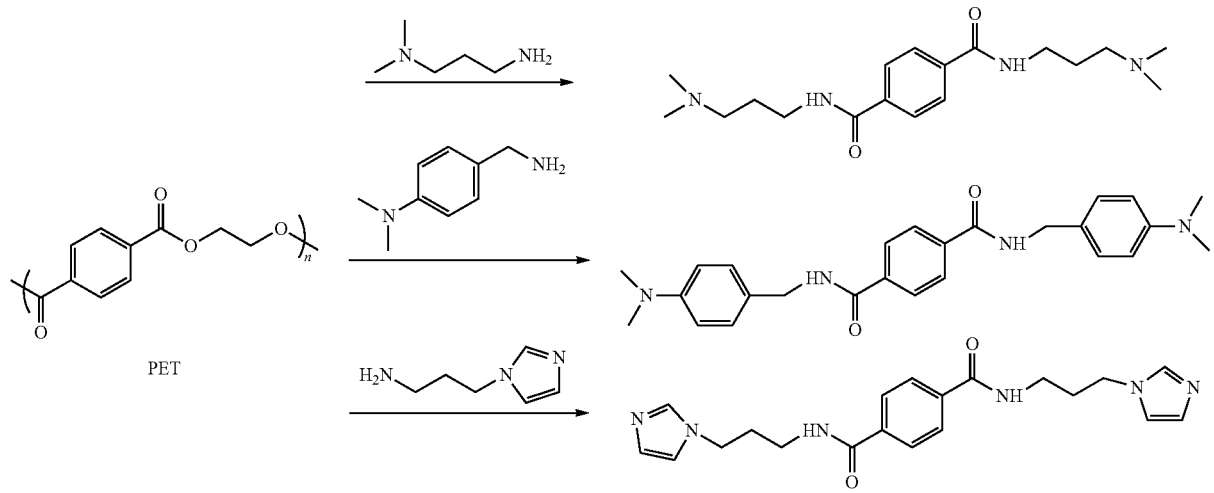

Scheme 1

Preparation of the plurality of degradable amine monomers (e.g., in accordance with Scheme 1) can be performed without the need of a catalyst and/or a solvent. Further, aminolysis of PET can be performed with an excess of the aminolysis reagents (e.g., four times excess of the aminolysis reagents). Moreover, the aminolysis can depolymerize PET at elevated temperatures. Upon cooling, the target degradable amine monomers can be crystallized from the excess reagent and an alcohol side product (e.g., ethylene glycol). The degradable amine monomers can then be filtered, rinsed (e.g., with ethylacetate), and used without need for further purification.

While Scheme 1 depicts three example degradable amine monomers derived from PET, other degradable amine monomers that can be derived from PET are also envisaged. For example, PET can be depolymerized with aminolysis reagents other than the three depicted in Scheme 1. For instance, any aminolysis reagent having a primary amino group and/or a secondary amino group, which can donate a hydrogen atom to facilitate bonding to the terephthalate structure, and a second amino group and/or imidazole group, which can later become a cation 104, can be polymerized with PET to prepare a degradable amine monomer for use at 402. Further, the prepared degradable amine monomers derived from PET, as described herein, can comprise the one or more amine monomers that can be utilized in method 700.

Additionally, in one or more embodiments the one or more amine monomers utilized in conjunction with method 700 can be derived from a molecule other than PET. One of ordinary skill in the art can readily recognize that a plethora of other starting molecules can be polymerized and/or depolymerized to prepare the one or more amine monomers (e.g., which can have degradable backbones, can comprise a terephthalamide structure, and/or can be a tetra-amine) that can be utilized in conjunction with the method 700.

The method 700 can optionally comprise stirring the one or more amine monomers, the one or more electrophiles, and the solvent at a temperature greater than or equal to 15° C. and less than or equal to 150° C. for a period of time greater than or equal to 8 hours and less than or equal to 72 hours (e.g., greater than or equal to 12 hours and less than or equal to 24 hours).

At 704, the method 700 can comprise forming one or more monomers from the one or more amine monomers and the one or more electrophiles. The monomer can comprise a single ionene unit 100 (e.g., characterized by chemical formula 600) that can comprise a cation 104 distributed along a degradable molecular backbone 102. The molecular backbone 102 can comprise a terephthalamide structure (e.g., as illustrated in chemical formula 600). Further, the single ionene unit 100 formed at 704 can have antimicrobial functionality. In one or more embodiments, the forming at 704 can be performed under nitrogen gas. Additionally, the forming at 704 can generate the cation through alkylation and/or quaternation with the one or more electrophiles. In various embodiments, the terephthalamide structure comprising the precipitate can be derived from the PET that was depolymerized to prepare the one or more amine monomers.

During the forming at 704, a nitrogen atom and/or a phosphorus atom located in the degradable amine monomers can be subject to alkylation and/or quaternization with the one or more electrophiles; thus, the forming at 704 can conduct a polymer-forming reaction (e.g., formation of the repeating ionene unit 100) and an installation of charge (e.g., forming a cation 104, including a nitrogen cation and/or a phosphorus cation) simultaneously without a need of a catalyst. Further, one or more hydrophobic functional groups 106 can be derived from the one or more electrophiles and/or can be bonded to degradable molecular backbone 102 (e.g., via one or more cations 104) as a result of the alkylation and/or quaternization process.

For example, the single ionene formed at 704 can comprise one or more embodiments of the ionene unit 100 and can be characterized by one or more embodiments of chemical formula 600. For instance, the single ionene unit 100 formed at 704 can comprise a degradable molecular backbone 102 that can comprise one or more cations 104 (e.g., represented by "X" in chemical formula 600), one or more linkage groups (e.g., represented by "Y" in chemical formula 600), one or more terephthalamide structures (e.g., as shown in FIG. 6), and/or one or more hydrophobic functional groups 106 (e.g., represented by "R" in chemical formula 600). The one or more cations 104 can be nitrogen cations (e.g., quaternary ammonium cations, imidazolium cations, and/or a combination thereof) and/or phosphorus cations (e.g., quaternary phosphonium cations). The cations 104 can be linked to the one or more terephthalamide structures via one or more linkage groups (e.g., alkyl groups and/or aryl groups). Further, one or more of the cations 104 can be bonded to one or more of the hydrophobic functional groups 106.

Antimicrobial activity of the repeating ionene units 100 generated by the method 700 can be independent of molecular weight. Thus, method 700 can target conditions that can extinguish molecular weight attainment by diffusion limited mechanism (e.g., polymer precipitation) to modest molecular weights (e.g., molecular weights less than 10,000 grams per mole (g/mol)), which can aid in the solubility of the one or more ionene units 100 in aqueous media.

Figure 8:
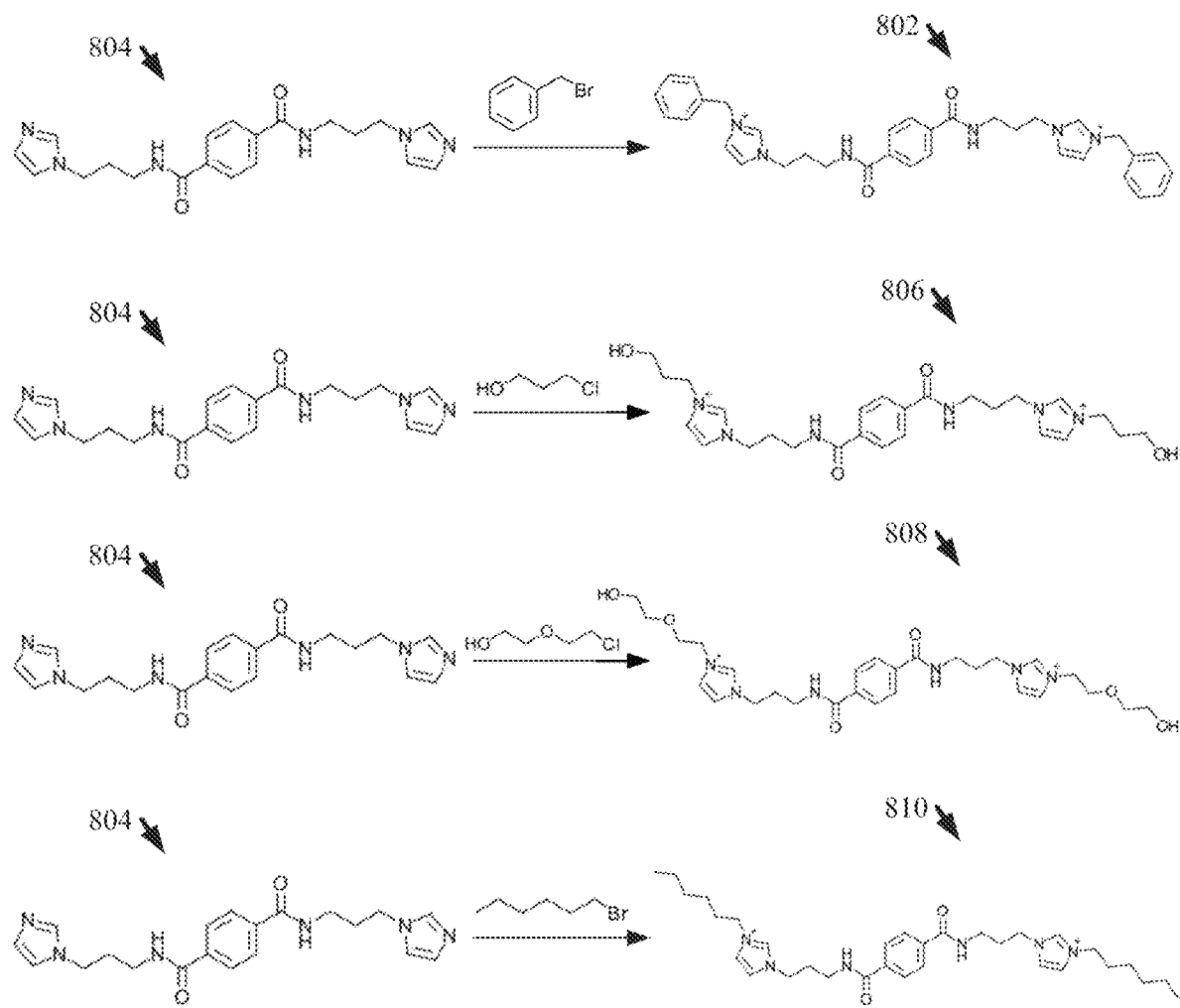
FIG. 8 illustrates a diagram of an example, non-limiting compound-forming schemes that can facilitate generating one or more ionene compositions in accordance with one or more embodiments described herein.

FIG. 8 illustrates a diagram of example, non-limiting compound-forming schemes that can facilitate generation of one or more ionene compositions (e.g., that can be characterized by chemical formula 600 and/or generated in accordance with method 700) in accordance with one or more embodiments described herein. Repetitive description of like elements employed in other embodiments described herein is omitted for sake of brevity. The ionene units 100 formed by generated by the compound-forming schemes of FIG. 8 can comprise one or more monomers. While one or more particular amine monomers and/or electrophiles are depicted; additional embodiments of the compound-forming schemes shown in FIG. 8 are also envisaged. For example, the principal mechanisms of the compound-forming schemes shown in FIG. 8 can be applied to any amine monomer and/or electrophile in accordance with the various features described herein (e.g., with reference to chemical formula 600 and/or method 700).

As shown in FIG. 8, the compound-forming schemes can depict generating ionene compositions (e.g., twenty-sixth ionene composition 802, twenty-seventh ionene composition 806, twenty-eighth ionene composition 808, and/or twenty-ninth ionene composition 810) from one or more alkyl halides (e.g., benzyl bromide; 3-chloro-1-propanol; 3-chloro-1,2-propanediol; and/or 1-bromohexane) and an amine monomer (e.g., fourth amine monomer 804). For example, the one or more alkyl halides (e.g., benzyl bromide; 3-chloro-1-propanol; 3-chloro-1,2-propanediol; and/or 1-bromohexane) can be dissolved with the amine monomer (e.g., fourth amine monomer 804) in solvent (e.g., DMF). The one or more alkyl halides (e.g., benzyl bromide; 3-chloro-1-propanol; 3-chloro-1,2-propanediol; and/or 1-bromohexane), the amine monomer (e.g., fourth amine monomer 804), and the solvent can be stirred at a temperature greater than or equal to 15° C. and less than or equal to 150° C. (e.g., room temperature ("RT")) for a period of time greater than or equal to 8 hours and less than or equal to 72 hours (e.g., greater than or equal to 12 hours and less than or equal to 24 hours).

The compound-forming schemes of FIG. 8 can covalently bond the one or more alkyl halides (e.g., benzyl bromide; 3-chloro-1-propanol; 3-chloro-1,2-propanediol; and/or 1-bromohexane) to the amine monomer (e.g., fourth amine monomer 804) through one or more amino groups (e.g., imidazole groups) of the amine monomers (e.g., fourth amine monomer 804). For example, the compound-forming schemes of FIG. 8 can comprise an alkylation of the one or more amino groups (e.g., imidazole groups) with the electrophile (e.g., benzyl bromide; 3-chloro-1-propanol; 3-chloro-1,2-propanediol; and/or 1-bromohexane) to form the ionene composition (e.g., twenty-sixth ionene composition 802, twenty-seventh ionene composition 806, twenty-eighth ionene composition 808, and/or twenty-ninth ionene composition 810) comprising a plurality of cations 104 (e.g., imidazolium cations). Further, the ionene composition (e.g., twenty-sixth ionene composition 802, twenty-seventh ionene composition 806, twenty-eighth ionene composition 808, and/or twenty-ninth ionene composition 810) can comprise one or more hydrophobic functional groups 106 derived from the one or more electrophiles (e.g., benzyl bromide; 3-chloro-1-propanol; 3-chloro-1,2-propanediol; and/or 1-bromohexane) as a result of the alkylation. Thus, the ionene compositions (e.g., twenty-sixth ionene composition 802, twenty-seventh ionene composition 806, twenty-eighth ionene composition 808, and/or twenty-ninth ionene composition 810) that can be generated by the compound-forming schemes of FIG. 8 can comprise the various features described in reference to FIGS. 1A-1B and/or chemical formula 600, and/or can be generated in accordance with the various features of method 700.

Figure 9:
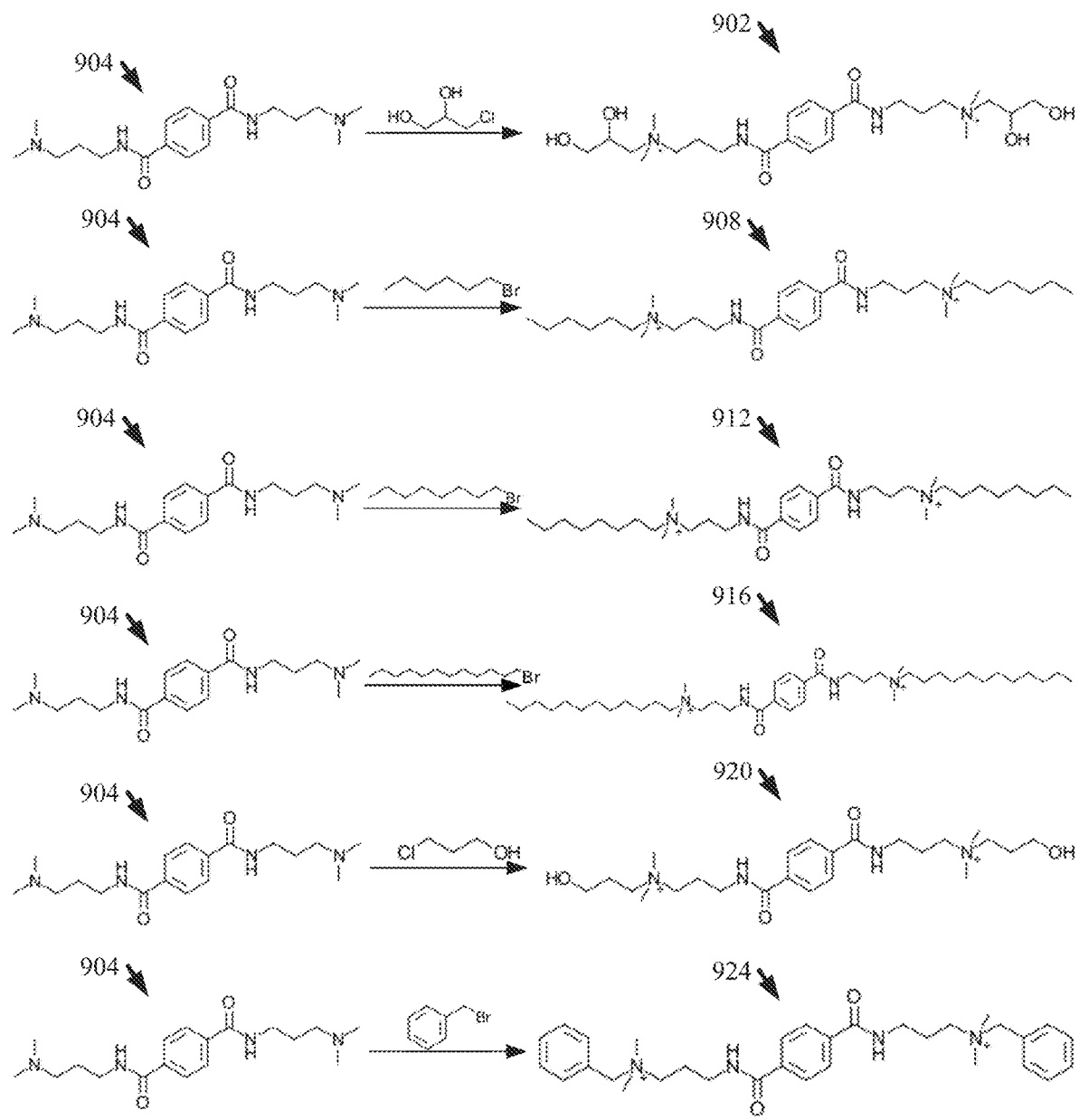
FIG. 9 illustrates a diagram of an example, non-limiting compound-forming schemes that can facilitate generating one or more ionene compositions in accordance with one or more embodiments described herein.

FIG. 9 illustrates a diagram of example, non-limiting compound-forming schemes that can facilitate generation of one or more ionene compositions (e.g., that can be characterized by chemical formula 600 and/or generated in accordance with method 700) in accordance with one or more embodiments described herein. Repetitive description of like elements employed in other embodiments described herein is omitted for sake of brevity. The ionene units 100 formed by generated by the compound-forming schemes of FIG. 9 can comprise one or more monomers. While one or more particular amine monomers and/or electrophiles are depicted; additional embodiments of the compound-forming schemes shown in FIG. 9 are also envisaged. For example, the principal mechanisms of the compound-forming schemes shown in FIG. 9 can be applied to any amine monomer and/or electrophile in accordance with the various features described herein (e.g., with reference to chemical formula 600 and/or method 700).

As shown in FIG. 9, the compound-forming schemes can depict generating ionene compositions (e.g., thirtieth ionene composition 902, thirty-first ionene composition 908, thirty-second ionene composition 912, thirty-third ionene composition 916, thirty-fourth ionene composition 920, and/or thirty-fifth ionene composition 924) from one or more alkyl halides (e.g., 3-chloro-1,2-propanediol; 1-bromohexane; 1-bromooctane; 1-bromododecane; 3-chloro-1-propanol; and/or benzyl bromide) and an amine monomer (e.g., fifth amine monomer 904). For example, the one or more alkyl halides (e.g., 3-chloro-1,2-propanediol; 1-bromohexane; 1-bromooctane; 1-bromododecane; 3-chloro-1-propanol; and/or benzyl bromide) can be dissolved with the amine monomer (e.g., fifth amine monomer 904) in solvent (e.g., DMF). The one or more alkyl halides (e.g., 3-chloro-1,2-propanediol; 1-bromohexane; 1-bromooctane; 1-bromododecane; 3-chloro-1-propanol; and/or benzyl bromide), the amine monomer (e.g., fifth amine monomer 904), and/or the solvent can be stirred at a temperature greater than or equal to 15° C. and less than or equal to 150° C. (e.g., room temperature ("RT")) for a period of time greater than or equal to 8 hours and less than or equal to 72 hours (e.g., greater than or equal to 12 hours and less than or equal to 24 hours).

The compound-forming schemes of FIG. 9 can covalently bond the one or more alkyl halides (e.g., 3-chloro-1,2-propanediol; 1-bromohexane; 1-bromooctane; 1-bromododecane; 3-chloro-1-propanol; and/or benzyl bromide) to the amine monomer (e.g., fifth amine monomer 904) through one or more amino groups (e.g., tertiary groups) of the amine monomers (e.g., fifth amine monomer 904). For example, the compound-forming schemes of FIG. 9 can comprise a quaternization of the one or more amino groups (e.g., tertiary groups) with the electrophile (e.g., 3-chloro-1,2-propanediol; 1-bromohexane; 1-bromooctane; 1-bromododecane; 3-chloro-1-propanol; and/or benzyl bromide) to form the ionene composition (e.g., thirtieth ionene composition 902, thirty-first ionene composition 908, thirty-second ionene composition 912, thirty-third ionene composition 916, thirty-fourth ionene composition 920, and/or thirty-fifth ionene composition 924) comprising a plurality of cations 104 (e.g., quaternary ammonium cations). Further, the ionene composition (e.g., thirtieth ionene composition 902, thirty-first ionene composition 908, thirty-second ionene composition 912, thirty-third ionene composition 916, thirty-fourth ionene composition 920, and/or thirty-fifth ionene composition 924) can comprise one or more hydrophobic functional groups 106 derived from the one or more electrophiles (e.g., 3-chloro-1,2-propanediol; 1-bromohexane; 1-bromooctane; 1-bromododecane; 3-chloro-1-propanol; and/or benzyl bromide) as a result of the quaternization. Thus, the ionene compositions (e.g., thirtieth ionene composition 902, thirty-first ionene composition 908, thirty-second ionene composition 912, thirty-third ionene composition 916, thirty-fourth ionene composition 920, and/or thirty-fifth ionene composition 924) that can be generated by the compound-forming schemes of FIG. 9 can comprise the various features described in reference to FIGS. 1A-1B and/or chemical formula 600, and/or can be generated in accordance with the various features of method 700.

FIG. 10 illustrates a diagram of an example, non-limiting chart 1000 that can depict the antimicrobial efficacy of one or more ionene compositions in accordance with one or more embodiments described herein. Repetitive description of like elements employed in other embodiments described herein is omitted for sake of brevity. To demonstrate the antimicrobial effects of the ionenes described herein (e.g., ionene units 100 that can comprise the various features described in reference to FIG. 1A-1B, and/or generated in accordance with one or more features regarding method 200 and/or the compound-forming schemes of FIG. 3, such as the ionene compositions depicted in FIGS. 4-5), a plurality of ionene compositions were evaluated against a broad spectrum of pathogens.

The first column 1002 of chart 1000 can depict the ionene composition subject to evaluation. The second column 1004 of chart 1000 can depict the minimum inhibitory concentration (MIC) in micrograms per milliliter (μg/mL) of the subject ionene composition regarding *Staphylococcus aureus* ("SA"). The third column 1006 of chart 1000 can depict the MIC in μg/mL of the subject ionene composition regarding *Escherichia coli* ("EC"). The fourth column 1008 of chart 1000 can depict the MIC in μg/mL of the subject ionene composition regarding *Pseudomonas aeruginosa* ("PA"). The fifth column 1010 of chart 1000 can depict the MIC in μg/mL of the subject polyionene composition regarding *Candida albicans* ("CA"). The sixth column 1012 of chart 1000 can depict the hemolytic activity ("HC$_{50}$") in μg/mL of the subject polyionene composition regarding rat red blood cells.

Figure 11:
FIG. 11 illustrates another diagram of an example, non-limiting chart that can depict antimicrobial functionality of various ionene compositions in accordance with one or more embodiments described herein.

FIG. 11 illustrates a diagram of an example, non-limiting chart 1100 that can depict the antimicrobial efficacy of one or more ionene compositions in accordance with one or more embodiments described herein. Repetitive description of like elements employed in other embodiments described herein is omitted for sake of brevity. To demonstrate the antimicrobial effects of the ionenes described herein (e.g., ionene units 100 that can comprise the various features described in reference to FIG. 1A-1B, and/or generated in accordance with one or more features regarding method 200 and/or the compound-forming schemes of FIG. 3, such as the ionene compositions depicted in FIG. 5), a plurality of ionene compositions were evaluated against a broad spectrum of pathogens.

The first column 1102 of chart 1100 can depict the ionene composition subject to evaluation. The second column 1104 of chart 1100 can depict the minimum inhibitory concentration (MIC) in micrograms per milliliter (μg/mL) of the subject ionene composition regarding *Staphylococcus aureus* ("SA"). The third column 1106 of chart 1100 can depict the MIC in μg/mL of the subject ionene composition regarding *Escherichia coli* ("EC"). The fourth column 1108 of chart 1100 can depict the MIC in μg/mL of the subject ionene composition regarding *Pseudomonas aeruginosa* ("PA"). The fifth column 1110 of chart 1100 can depict the MIC in μg/mL of the subject polyionene composition regarding *Candida albicans* ("CA"). The sixth column 1112 of chart 1100 can depict the hemolytic activity ("HC$_{50}$") in μg/mL of the subject polyionene composition regarding rat red blood cells.

Figure 12:
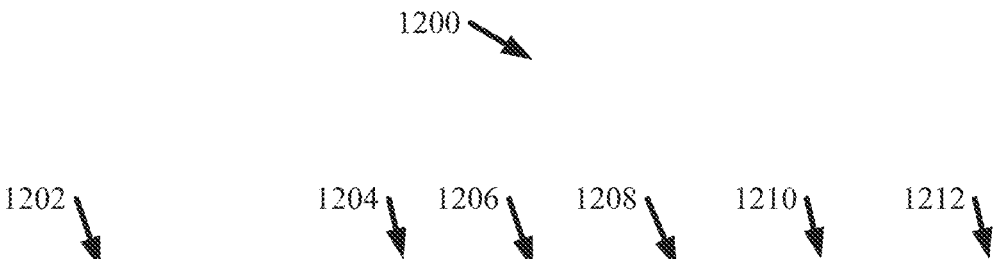
FIG. 12 illustrates another diagram of an example, non-limiting chart that can depict antimicrobial functionality of various ionene compositions in accordance with one or more embodiments described herein.

FIG. 12 illustrates a diagram of an example, non-limiting chart 1200 that can depict the antimicrobial efficacy of one or more ionene compositions in accordance with one or more embodiments described herein. Repetitive description of like elements employed in other embodiments described herein is omitted for sake of brevity. To demonstrate the antimicrobial effects of the ionenes described herein (e.g., ionene units 100 that can comprise the various features of chemical formula 600, and/or generated in accordance with one or more features regarding method 700 and/or the compound-forming schemes of FIGS. 8 and/or 9), a plurality of ionene compositions were evaluated against a broad spectrum of pathogens.

The first column 1202 of chart 1200 can depict the ionene composition subject to evaluation. The second column 1204 of chart 1200 can depict the minimum inhibitory concentration (MIC) in micrograms per milliliter (μg/mL) of the subject ionene composition regarding *Staphylococcus aureus* ("SA"). The third column 1206 of chart 1200 can depict the MIC in μg/mL of the subject ionene composition regarding *Escherichia coli* ("EC"). The fourth column 1208 of chart 1200 can depict the MIC in μg/mL of the subject ionene composition regarding *Pseudomonas aeruginosa* ("PA"). The fifth column 1210 of chart 1200 can depict the MIC in μg/mL of the subject polyionene composition regarding *Candida albicans* ("CA"). The sixth column 1212 of chart 1200 can depict the hemolytic activity ("HC$_{50}$") in μg/mL of the subject polyionene composition regarding rat red blood cells.

Figure 13A:
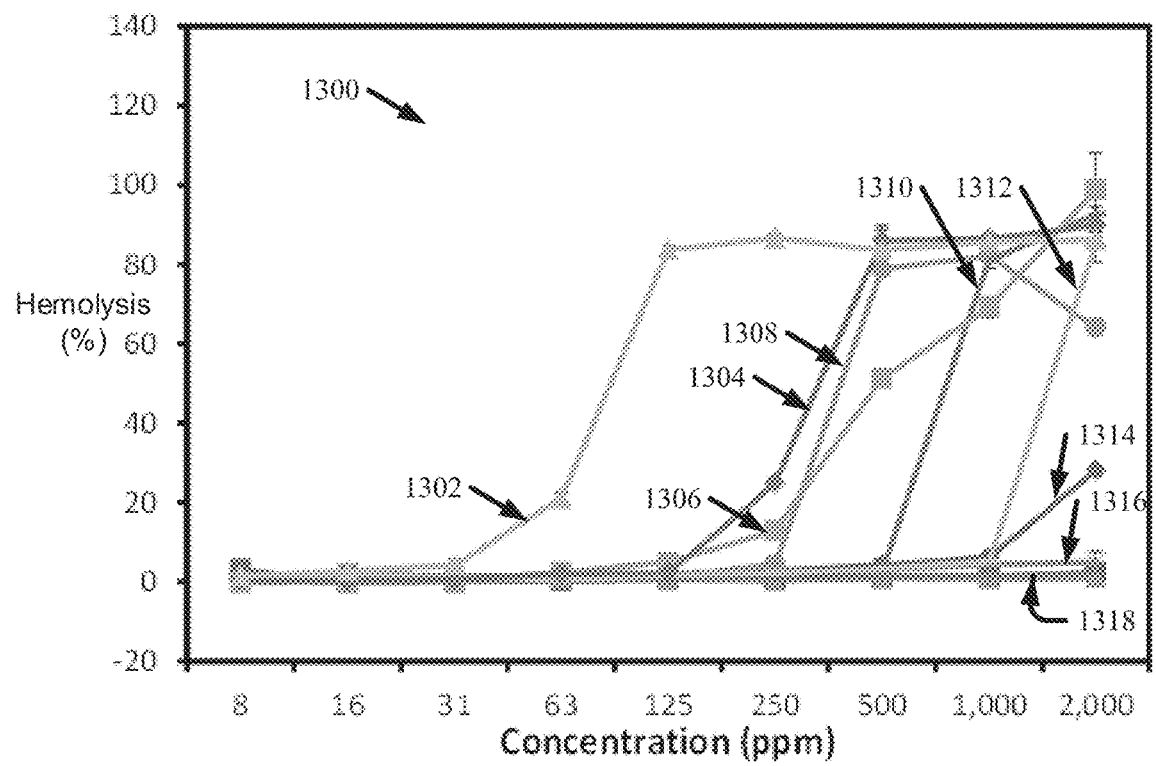
FIG. 13A illustrates a diagram of an example, non-limiting graph that can depict hemolysis activity of various ionene composition in accordance with one or more embodiments described herein.

FIG. 13A illustrates a diagram of an example, non-limiting graph 1300 that can depict the hemolytic activity of various ionene compositions at various concentrations in accordance with the one or more embodiments described herein. Repetitive description of like elements employed in other embodiments described herein is omitted for sake of brevity. For example, FIG. 13A shows the hemolytic activity of various ionene compositions at concentrations ranging from 8 parts per million (ppm) to 2000 ppm. The hemolytic activity depicted in graph 1300 can regard rat red blood cells.

The first line 1302 of graph 1300 can represent the twenty-fifth ionene composition 522. The second line 1304 of graph 1300 can represent the twenty-fourth ionene composition 520. The third line 1306 can represent the third ionene composition 316. The fourth line 1308 of graph 1300 can represent the eighteenth ionene composition 508. The fifth line 1310 of graph 1300 can represent the twenty-second ionene composition 516. The sixth line 1312 of graph 1300 can represent the twenty-third ionene composition 518. The seventh line 1314 of graph 1300 can represent the seventeenth ionene composition 506. The seventh line 1316 of graph 1300 can represent twentieth ionene composition 512. The eighth line 1318 of graph 1300 represent the twenty-first ionene composition 514, the nineteenth ionene composition 510, and/or the sixteenth ionene composition 504.

Figure 13B:
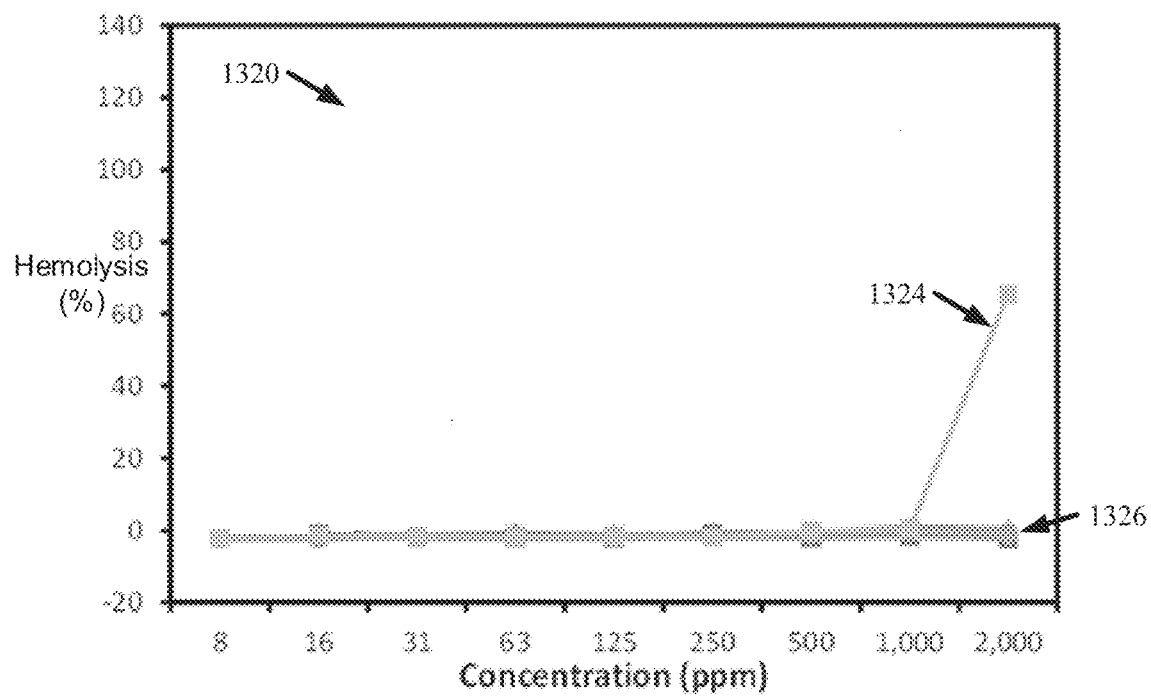
FIG. 13B illustrates another diagram of an example, non-limiting graph that can depict hemolysis activity of various ionene composition in accordance with one or more embodiments described herein.

FIG. 13B illustrates a diagram of an example, non-limiting graph 1320 that can depict the hemolytic activity of various ionene compositions at various concentrations in accordance with the one or more embodiments described herein. Repetitive description of like elements employed in other embodiments described herein is omitted for sake of brevity. For example, FIG. 13B shows the hemolytic activity of various ionene compositions at concentrations ranging from 8 parts per million (ppm) to 2000 ppm. The hemolytic activity depicted in graph 1320 can regard rat red blood cells.

The first line 1324 of graph 1320 can represent the fourteenth ionene composition 422. The second line 1326 of graph 1320 can represent the fourth ionene composition 402, the fifth ionene composition 404, the sixth ionene composition 406, the seventh ionene composition 408, the eighth ionene composition 410, the ninth ionene composition 412, the tenth ionene composition 414, the twelfth ionene composition 418, and/or the thirteenth ionene composition 420.

Figure 14:
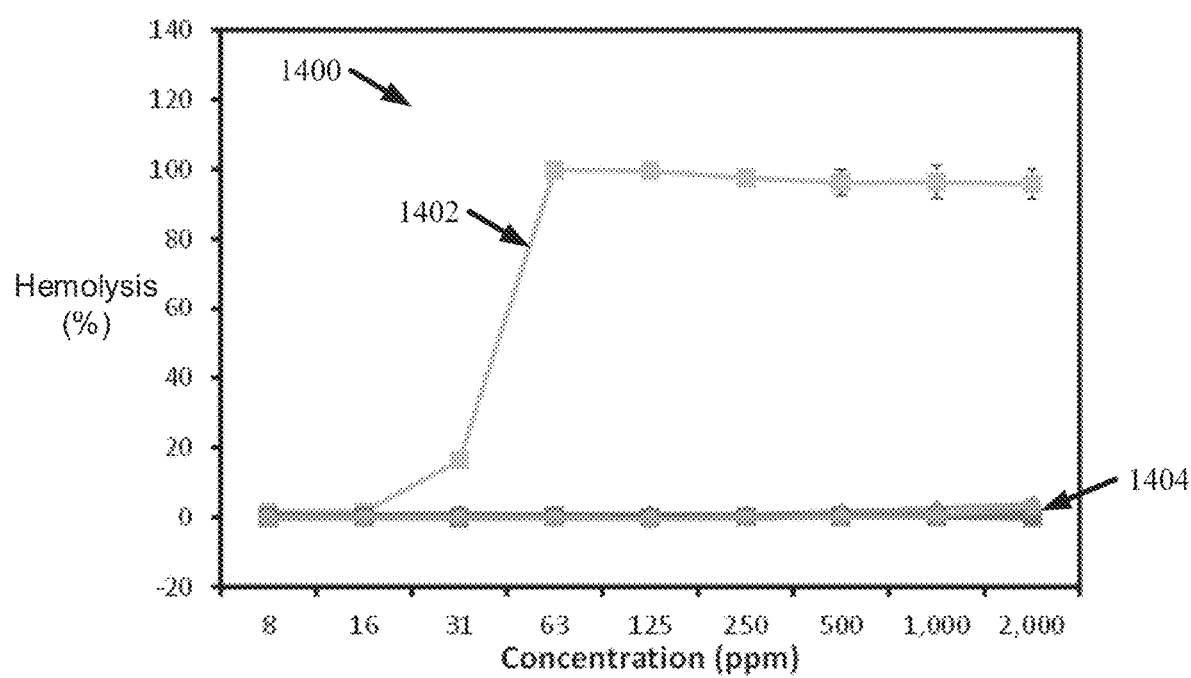
FIG. 14 illustrates another diagram of an example, non-limiting graph that can depict hemolysis activity of various ionene composition in accordance with one or more embodiments described herein.

FIG. 14 illustrates a diagram of an example, non-limiting graph 1400 that can depict the hemolytic activity of various ionene compositions at various concentrations in accordance with the one or more embodiments described herein. Repetitive description of like elements employed in other embodiments described herein is omitted for sake of brevity. For example, FIG. 14 shows the hemolytic activity of various ionene compositions at concentrations ranging from 8 parts per million (ppm) to 2000 ppm. The hemolytic activity depicted in graph 1400 can regard rat red blood cells.

The first line 1402 of graph 1400 can represent the thirty-third ionene composition 916. The second line 1404 of graph 1400 can represent the twenty-sixth ionene composition 802, the twenty-seventh ionene composition 806, the twenty-eighth ionene composition 808, the twenty-ninth ionene composition 810, the thirtieth ionene composition 902, the thirty-first ionene composition 908, the thirty-second ionene composition 912, the thirty-fourth ionene composition 920, and/or the thirty-fifth ionene composition 924.

FIG. 15 illustrates another flow diagram of an example, non-limiting method 1500 of killing a pathogen, preventing the growth of a pathogen, and/or preventing contamination by a pathogen. Repetitive description of like elements employed in other embodiments described herein is omitted for sake of brevity. Example pathogens include, but are not limited to: Gram-negative bacteria, Gram-positive bacteria, fungi, yeast, a combination thereof, and/or the like.

At 1502, the method 1500 can comprise contacting the pathogen with one or more monomers, which can comprise a single ionene unit 100. The one or more single ionene units 100 can comprise one or more cations 104 distributed along a molecular backbone 102. Also, the one or more single ionene units 100 can comprise one or more hydrophobic functional groups 106 covalently bonded to the molecular backbone 102 (e.g., via the one or more cations 104). The one or more cations 104 can be nitrogen cations and/or phosphorus cations. Example nitrogen cations can include, but are not limited to: protonated secondary amine cations, protonated tertiary amine cations, quaternary ammonium cations, and/or imidazolium cations. In one or more embodiments, the molecular backbone 102 can comprise one or more terephthalamide structures. The one or more monomers can comprise ionene compositions in accordance with the various embodiments described herein (e.g., the various features described regarding FIG. 1-9).

At 1504, the method 1500 can comprise electrostatically disrupting a membrane of the pathogen upon contacting the pathogen with the monomer. The membrane can comprise a phospholipid bilayer 110. The one or more cations 104 comprising the single ionene unit 100 can target and/or disrupt the pathogen's membrane in accordance with the lysis process 108. Additionally, the method 1500 can comprise destabilizing the membrane of the pathogen by integration of the ionene unit's 100 one or more hydrophobic functional groups 106 into the membrane.

The various structures (e.g., described regarding FIGS. 1A, 1B, and/or 6), compositions (e.g., described regarding FIGS. 3-5, 8-14), and/or methods (e.g., described regarding FIGS. 2, 7, and/or 15) described herein can be incorporated into a variety of applications. For example, said applications can include cleaning, sanitizing, disinfecting, and/or otherwise treating various articles such as, but not limited to: food packaging, medical devices, floor surfaces, furniture surfaces, wound care instruments (e.g., bandages and/or gauss), building surfaces, plants (e.g., agricultural crops), ground surfaces, farming equipment, beds, sheets, clothes, blankets, shoes, doors, door frames, walls, ceilings, mattresses, light fixtures, facets, switches, sinks, grab rails, remote controls, vanities, computer equipment, carts, trolleys, hampers, bins, a combination thereof, and/or the like. In another example, said applications can include pharmaceuticals, pharmaceutical salts, hygiene products (e.g., soaps and/or shampoos), and/or the like. In a further example, said applications can include agricultural sprays and/or aqueous solutions that can facilitate processing crops for consumption.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, compositions, and methods. It is, of course, not possible to describe every conceivable combination of reagents, products, solvents, and/or articles for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A monomer comprising:
a single ionene unit comprising a nitrogen cation distributed along a molecular backbone, and a hydrophobic functional group covalently bonded to the molecular backbone, wherein the single ionene unit has antimicrobial functionality, wherein the monomer is characterized by a chemical structure selected from the group consisting of:

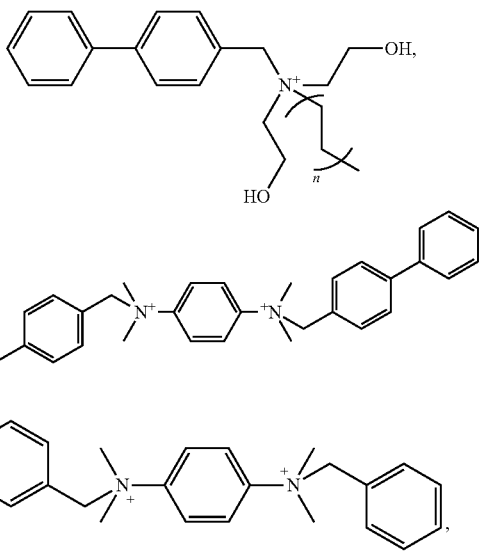

21
-continued

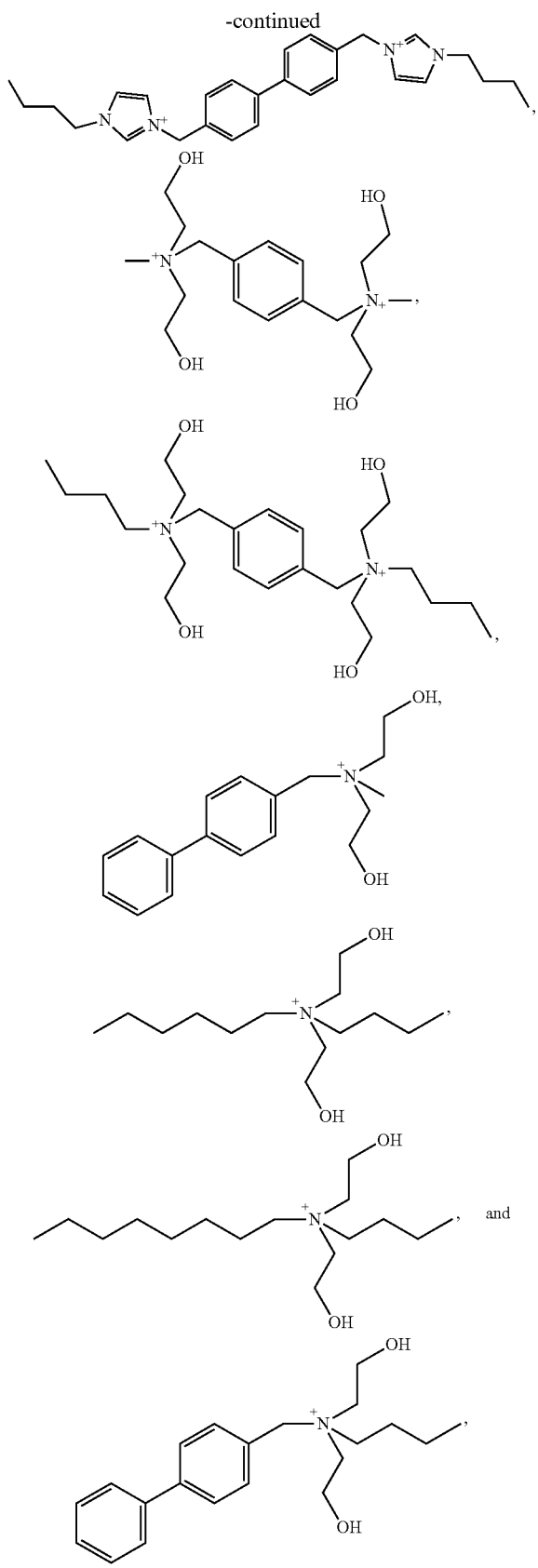

wherein "n" is an integer greater than or equal to one and less than or equal to one thousand.

22

2. The monomer of claim 1, wherein the hydrophobic functional group is derived from an alkyl halide.

3. A method for making the monomer of claim 1, comprising:

dissolving an amine monomer and an electrophile in a solvent, wherein the amine monomer is characterized by a first structure:

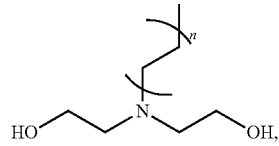

wherein "n" is an integer greater than or equal to one and less than or equal to one thousand, and wherein the electrophile is a halide compound characterized by a first formula:

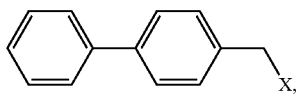

wherein "X" is a halogen; and forming a monomer from the amine monomer and the electrophile, the monomer comprising a single ionene unit, and the single ionene unit comprising a nitrogen cation distributed along a molecular backbone, and a hydrophobic functional group covalently bonded to the molecular backbone, wherein the single ionene unit has antimicrobial functionality, and wherein the monomer is characterized by second formula:

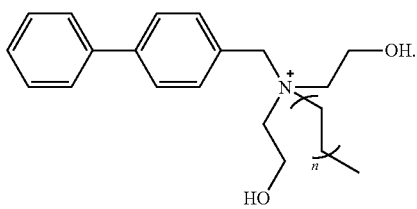

4. The method of claim 3, wherein the forming comprises a quaternization to form the nitrogen cation, and wherein the halogen is selected from the group consisting of bromide and chloride.

5. The method of claim 4, wherein the method further comprises:

stirring the amine monomer, the electrophile, and the solvent at a temperature greater than or equal to 15 degrees Celsius (° C.) and less than or equal to 150° C. for a defined period of time greater than or equal to 12 hours and less than or equal to 24 hours.

6. A method for making the monomer of claim 1, comprising:

dissolving an amine monomer and an electrophile in a solvent, wherein the amine monomer is characterized by a first structure:

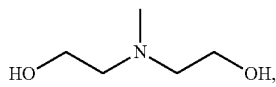

wherein the electrophile is a halide compound characterized by a second structure selected from the group consisting of:

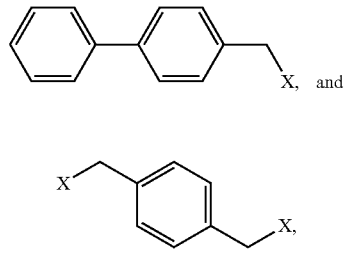

wherein "X" is a halogen; and forming a monomer from the amine monomer and the electrophile, the monomer comprising a single ionene unit, and the single ionene unit comprising a nitrogen cation distributed along a molecular backbone, and a hydrophobic functional group covalently bonded to the molecular backbone, wherein the single ionene unit has antimicrobial functionality, and wherein the monomer is characterized by a third structure selected from the group consisting of:

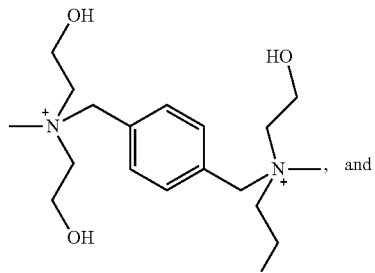

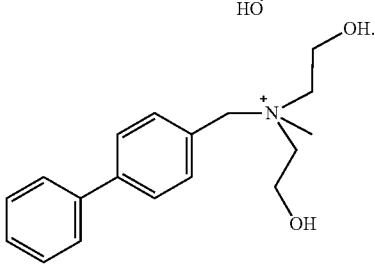

7. The method of claim 3, wherein the forming comprises a quaternization to form the nitrogen cation, and wherein the halogen is selected from the group consisting of bromide and chloride.

8. The method of claim 4, wherein the method further comprises:
stirring the amine monomer, the electrophile, and the solvent at a temperature greater than or equal to 15 degrees Celsius (° C.) and less than or equal to 150° C. for a defined period of time greater than or equal to 12 hours and less than or equal to 24 hours.

* * * * *